(12) United States Patent
Gines et al.

(10) Patent No.: US 7,424,141 B2
(45) Date of Patent: Sep. 9, 2008

(54) SYSTEM AND METHOD FOR PERFORMING AUTO-FOCUSED TOMOSYNTHESIS

(75) Inventors: David Gines, Fort Collins, CO (US); Tracy K. Ragland, Boulder, CO (US); John M. Heumann, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 853 days.

(21) Appl. No.: 10/651,667

(22) Filed: Aug. 29, 2003

(65) Prior Publication Data

US 2005/0047636 A1    Mar. 3, 2005

(51) Int. Cl.
 *G06K 9/00* (2006.01)
(52) U.S. Cl. ..................................... 382/131
(58) Field of Classification Search ................ 382/128, 382/131, 240
See application file for complete search history.

(56) References Cited

U.S. PATENT DOCUMENTS

| | | | |
|---|---|---|---|
| 4,926,452 | A | 5/1990 | Baker et al. |
| 5,461,655 | A | 10/1995 | Vuylsteke et al. |
| 5,841,890 | A | 11/1998 | Kraske |
| 5,953,388 | A | 9/1999 | Walnut et al. |
| 6,002,739 | A | 12/1999 | Heumann |
| 6,178,223 | B1 | 1/2001 | Solomon et al. |
| 6,201,850 | B1 | 3/2001 | Heumann |
| 6,351,548 | B1 | 2/2002 | Basu et al. |
| 6,510,241 | B1 * | 1/2003 | Vaillant et al. .............. 382/154 |
| 6,611,627 | B1 * | 8/2003 | LaRossa et al. ............. 382/240 |
| 6,768,782 | B1 * | 7/2004 | Hsieh et al. .................... 378/8 |

OTHER PUBLICATIONS

"Multiresolution Tomographic Reconstruction Using Wavelets", Delaney et al, IEEE Trans. On Image Processing, vol. 4, No. 6, Jun. 1995.*
"A Fast Tomographic Reconstruction Algorithm in the 2-D Wavlet Transformation Domain", Blanc-Feraud, L et al, 1994 International Conference on Acoustics, Speech, and Signal Processing, vol. V, Apr. 19-22, 1994, pp. v305-v308.*
Beylkin, G. et al., "Fast Wavelet Transforms and Numerical Algorithms I", Comm. Pure and Appl. Math, vol. 44, pp. 141-183, 191.
Bhatia, M. et al., "Wavelet Based Methods for Multicate Tomographic Reconstruction", Engineering in Medicine and Biology Society Proceedings, vol. 1, pp. 2a-3a, 1994.
Bronnikov, A. et al., "Wacelet-based image enhancement in x-ray imaging and tomography", Applied Optics, vol. 37, No. 20, pp. 4437-4448, Jul. 1998.

(Continued)

*Primary Examiner*—Tom Y Lu

(57) ABSTRACT

A system and method for performing auto-focusing operations for tomosynthetic reconstruction of images are provided. More specifically, embodiments of the present invention provide a system and method for efficiently computing the gradient of one or more depth layers of an object under inspection, wherein such gradients may be used in performing auto-focusing operations to determine a depth layer that includes an in-focus view of a feature that is of interest. In at least one embodiment, a method is provided that comprises capturing detector image data for an object under inspection, and using the detector image data for computing gradient information for at least one depth layer of the object under inspection without first tomosynthetically reconstructing a full image of the at least one depth layer.

26 Claims, 12 Drawing Sheets

OTHER PUBLICATIONS

Daubechies, I. "Orthonormal Bases of Compactly Supported Wavelets", Comm. Pure and Appl. Math, vol. 41, pp. 909-996, 1988.

Destefano, J. et al., "Wavelet Localization of the Radon Transform in Even Dimensions", Proc. IEEE-SP Int'l. Symposium, pp. 137-140, Oct. 1999.

Donoho, D. et al., "Nonlinear Solution of Linear Inverse Problems by Wavelet-Vaguelette Decomposition", Applied and Computational Harmonic Analysis, vol. 2, Issue 2, pp. 1-46, Apr. 1995.

Harpen, M.D. "A Computer Simulation of Wavelet Noise Reduction in Computed Tomography", Medical Physics, vol. 26, Issue 8, pp. 1600-1606, Aug. 1999.

Kolaczyk, E. "Wavelet Shrinkage in Tomography", Engineering in Medicine and Biology Society, Proc. 16th Ann. Int'l. Conf. of the IEEE, vol. 2, pp. 1206-1207, 1994.

Lee, N. et al., "Wavelet Methods for Inverting the Radon Transform with Noisy Data", IEEE Transactions on Image Processing, vol. 10, Issue 1, pp. 79-94, Jan. 2001.

Mallat, S. "A Theory for Multiresolution Signal Decomposition: The Wavelet Representation", IEEE Transactions on Pattern Analysis and Machine Intelligence, vol. 11, Issue 7, pp. 674-6936, 1989.

Nath, S. et al., "Wavelet based compression and denoising of optical tomography data", Optics Communications, vol. 167, Issues 1-6, pp. 37-46, Aug. 15, 1999.

Olson, T. "Limited Angle Tomography Via Multiresolution Analysis and OVersampling", Proceedings of the IEEE-SP Int'l. Symposium, pp. 215-218, Oct. 1992.

Olson, T. et al., "Wavelet Localization of the Radon Transform", IEEE Transactions on Signal Prfocessing, vol. 42, Issue 8, pp. 2055-2067 1994.

Rashid-Farrokhi, F. et al., "Wavelet-Based Multisolution Local Tomography", IEEE Transactions on Image Processing, vol. 6, Issue 10, pp. 1412-1430, 1997.

Sahiner, B. et al., "On the Use of Wavelets in Inverting the Radn Transform", Nuclear Science Symposium and Medical Imaging conference, IEEE, vol. 2, pp. 1129-1131, Oct. 1992.

Sahiner, B. et al., Limited Angle Tomography Using Wavelets, Nuclear Science Symposium and Medical Imaging Conference, vol. 3, pp. 1912-1916, Oct. 1993.

Warrick, A. et al., "A Wavelet Localized Radon Transform", Proc. of SPIE—The Int'l. Soc. for Optical Engineering, vol. 2569, Part 2, pp. 632-643, 1995.

Warrick A. et al., "A Wavelet Localized Radon Transform Based Detector for a Signal with Unknown Parameters", Signals, Systems and Computers, vol. 2, pp. 860-864, Oct. 1995.

Yagle, A. "Region-of-Interest Tomography Using the Wavelet Transform and Angular Harmonics", Image Processing Proceedings, vol. 2, pp. 461-463, Oct. 1995.

Zhu, W. et al., "A Wavelet-Based Multiresolution Regularized least Squares Recontruction Approach for Optical Tomography", IEEE Transactions on Medical Imaging, vol. 16, Issue 2, pp. 210-217, 1997.

* cited by examiner

SYSTEM AND METHOD FOR PERFORMING AUTO-FOCUSED TOMOSYNTHESIS

TECHNICAL FIELD

The present invention relates in general to image processing, and more particularly to a system and method for efficiently computing gradient information which may be used for performing auto-focusing for tomosynthetic reconstruction of images.

BACKGROUND OF THE INVENTION

It is often desired to construct a cross-sectional view (layer or slice) and/or three-dimensional (3D) view of an object for which actually presenting such views is difficult or impossible, such as due to irreparably damaging the object. For example, imaging systems are utilized in the medical arts to provide a view of a slice through a living human's body and to provide 3D views of organs therein. Similarly, imaging systems are utilized in the manufacture and inspection of industrial products, such as electronic circuit boards and/or components, to provide layer views and 3D views for inspection thereof.

Often, desired images are provided through reconstruction techniques which use multiple two-dimensional (2D) radiographic, e.g., X-band radiation (X-ray), images, e.g., detector images. The technique of reconstructing a desired image or view of an object (be it a 3D image, a cross-sectional image, and/or the like) from multiple projections (e.g., different detector images) is broadly referred to as tomography. When such reconstructing of a cross-sectional image is performed with the aid of a processor-based device (or "computer"), the technique is broadly referred to as computed (or computerized) tomography (CT). In a typical example application, a radiation source projects X-band radiation through an object onto an electronic sensor (or "detector") array thereby providing a detector image. By providing relative movement between one or more of the object, the source, and the sensor array, multiple views (multiple detector images having different perspectives) may be obtained. An image of a slice through the object or a 3D image of the object may then be approximated by use of proper mathematical transforms of the multiple views. That is, cross-sectional images of an object may be reconstructed, and in certain applications such cross-sectional images may be combined to form a 3D image of the object.

Within X-ray absorption tomography, a number of imaging techniques are applicable to reconstruction of cross-sectional slices. One imaging technique is known as laminography. In laminography, the X-ray source and sensor are moved in a coordinated fashion relative to the object to be viewed so that portions of an object outside a selected focal plane lead to a blurred image at the detector array. Focal plane images are reconstructed in an analog averaging process. Examples of laminography systems that may be utilized for electronics inspection are disclosed in U.S. Pat. No. 4,926,452 entitled "AUTOMATED LAMINOGRAPHY SYSTEM FOR INSPECTION OF ELECTRONICS" and in U.S. Pat. No. 6,201,850 entitled "ENHANCED THICKNESS CALIBRATION AND SHADING CORRECTION FOR AUTOMATIC X-RAY INSPECTION." An advantage of laminography is that extensive computer processing of ray equations is not required for image reconstruction.

Another imaging technique is known as tomosynthesis. Tomosynthesis is an approximation to laminography in which multiple projections (or views) are acquired and combined. As the number of views increases, the resulting combined image generally approaches that obtained using laminography with the same geometry. A differentiating feature of tomosynthesis from the above-described laminographic technique is that in tomosynthesis X-ray images obtained from different directions (different angles of view) can be manipulated (e.g., overlapped with different spatial shifts and their brightness averaged) to produce a variety of cross-sections. In other words, one set of X-ray images can be used to obtain multiple cross-sections of an object under inspection (e.g., cross-sections of the object at different heights). Tomosynthesis may be performed as an analog method, for example, by superimposing sheets of exposed film. Tomosynthesis may, instead, be performed as a digital method. In digital tomosynthesis, the individual views are divided into pixels, and digitized and combined via computer software.

Tomosynthesis is of particular interest for use in relatively high-speed applications in which images are desired to be reconstructed very quickly, e.g., in real-time. Examples of such high-speed applications include, without limitation, reconstructing images for medical applications and reconstructing images for automated inspection of industrial products. For instance, as medical procedures continue to evolve, certain medical applications are beginning to desire fast reconstruction of cross-sectional images. Real-time X-ray imaging is increasingly being desired by medical procedures, such as many electro-physiologic cardiac procedures, peripheral vascular procedures, percutaneous transluminal catheter angioplasty (PTCA) procedures, urological procedures, and orthopedic procedures, as examples. Additionally, reconstruction of cross-sectional images from radiographic (e.g., X-ray) images has been utilized in quality control inspection systems for inspecting a manufactured product, such as electronic devices (e.g., printed circuit boards). That is, tomosynthesis may be used in an automated inspection system to reconstruct images of one or more planes (which may be referred to herein as "depth layers" or "cross-sections") of an object under study in order to evaluate the quality of the object (or portion thereof). An X-ray imaging system may capture detector images (e.g., pixels) of a circuit board at various locations and at various orientations. Primarily, one is interested in images that lie in the same plane as the circuit board. In order to obtain these images at a given region of interest, raw X-ray detector images (pixels) may be mathematically processed using a reconstruction algorithm (e.g., Backprojection or shift-and-add algorithms) to reconstruct cross-sectional layers or slices.

For instance, a printed circuit board (or other object under study) may comprise various depth layers of interest for inspection. As a relatively simple example, a dual-sided printed circuit board may comprise solder joints on both sides of the board. Thus, each side of the circuit board on which the solder joints are arranged may comprise a separate layer of the board. Further, the circuit board may comprise surface mounts (e.g., a ball grid array of solder) on each of its sides, thus resulting in further layers of the board. The circuit board (or other object under study) may be imaged from various different angles of view (e.g., by exposure to X-rays at various different angles) resulting in radiographic images of the circuit board (e.g., pixel data), and such radiographic images may be processed to reconstruct an image of a layer (or "slice") of the circuit board. Thereafter, the resulting cross-sectional images may, in some inspection systems, be displayed layer by layer, and/or such cross-sectional images may be used to reconstruct a full 3D visualization of the object under inspection.

In laminography, only one layer may be reconstructed at a time. A potential advantage of tomosynthesis is that many different layers may be reconstructed from a given set of projection (detector) image data. Thus, the potential for more efficient reconstruction exists with tomosynthesis because a new set of image data need not be acquired for every layer of an area of an object to be reconstructed. However, while tomosynthesis allows for many different layers to be reconstructed from a given set of image data, only a few of those layers may be of interest, such as those corresponding to the top and bottom surfaces of a circuit board under inspection. The location of those layers of interest may be obtained in advance, as must be done in laminography, using an appropriate locating system, or, for tomosynthesis, may be done after data acquisition using an appropriate analysis of image layers. In the latter case, the selected image may be one that maximizes some constraint, such as image sharpness. When this analysis is automated using a processing unit, e.g. a digital computer, it is broadly referred to as "auto-focusing."

BRIEF SUMMARY OF THE INVENTION

Embodiments of the present invention provide a system and method for performing auto-focusing operations. More specifically, embodiments of the present invention provide a system and method for efficiently computing the gradient of one or more depth layers of an object under inspection, wherein such gradients may be used in performing auto-focusing operations to determine a depth layer that includes an in-focus view of a feature that is of interest.

In accordance with at least one embodiment, a method is provided that comprises capturing detector image data for at least a portion of an object under inspection. The method further comprises using the detector image data for computing gradient information for at least one depth layer of the at least a portion of the object under inspection without first tomosynthetically reconstructing a full image of the at least one depth layer.

In accordance with at least one embodiment, a system is provided that comprises an auto-focusing processor operable to compute a wavelet transform for a captured detector image of at least a portion of an object under inspection and use the wavelet transform to perform auto-focusing. The auto-focusing processor may, for example, comprise computer-executable software code for computing the wavelet transform, and a processor for executing the computer-executable software code.

In accordance with at least one embodiment, a system is provided that comprises means for capturing a detector image of at least a portion of an object under inspection. The system further comprises means for computing a wavelet transform for the captured detector image, and means for computing a gradient for at least one depth layer of the object under inspection from the wavelet transform.

In accordance with at least one embodiment, a method is provided that comprises capturing radiographic image data for at least a portion of an object under inspection. The method further comprises performing auto-focusing to determine, from a plurality of depth layers of the object under inspection in which a layer of interest potentially resides, the depth layer of interest, wherein the auto-focusing does not require fully reconstructing all of the plurality of depth layers.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1A:
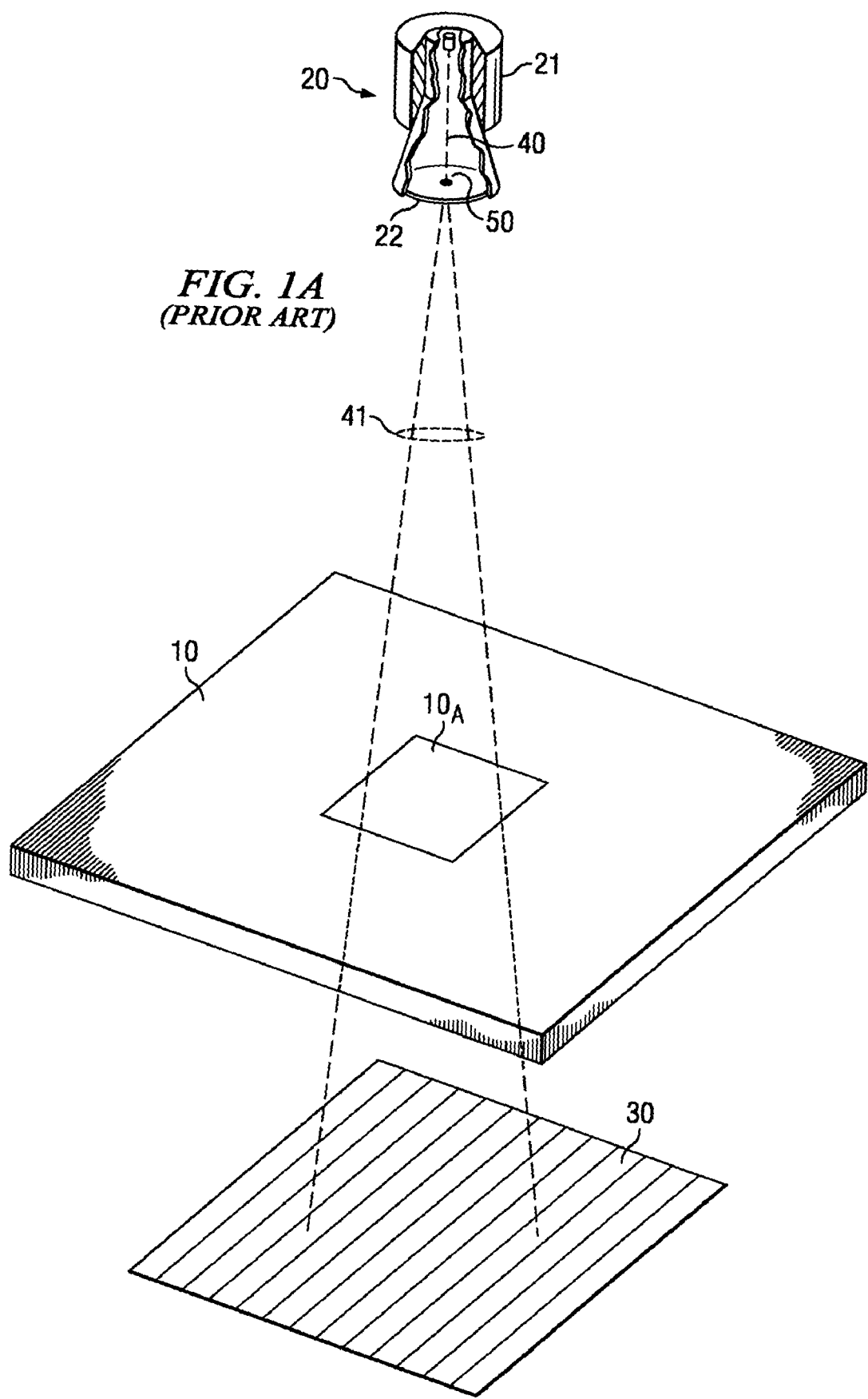
FIGS. 1A-1B show a schematic representation of an example digital tomosynthesis system geometry which may be used with embodiments of the present invention.

Embodiments of the present invention provide a system and method for auto-focusing in tomosynthesis. Auto-focusing techniques are provided that reduce the computational burden of the reconstruction process and image analysis. In accordance with embodiments of the present invention, full images of all layers of an object need not be reconstructed before determining the layer of focus. Rather, an auto-focusing technique is provided that enables identification of a layer of focus without requiring all layers of the object to first be reconstructed. Thus, because full images of all layers need not be reconstructed before the auto-focus technique determines the layer of focus, computational costs associated with the auto-focus and reconstruction processes may be reduced. For instance, certain layers that are not reconstructed before/during the auto-focus process and that are not determined to be the layer of focus need not be reconstructed at all.

In certain embodiments of the present invention, an auto-focus technique is provided that enables relatively coarse image resolution to be used in determining the layer of focus. That is, images having lower resolution than is desired for reconstruction may be used in performing auto-focus. In certain embodiments, a "progressive" or "hierarchical" auto-focus technique is provided that enables a low resolution image to be used to identify a region of layers in which the layer of focus resides, then use a higher resolution of layers within the identified region to progressively approach (or zone in on) the layer of focus.

Thus, in certain embodiments, a "multi-level" or "multi-resolution" auto-focus algorithm is provided that reconstructs images on a plurality of levels or resolutions. In particular, coarse-resolution representations of the projection (detector) images may be used to generate an initial analysis of the sharpness of layers. Once a collection of layers has been identified as possibly being the sharpest using this analysis, a fine-resolution analysis may be used to refine the estimated location of the sharpest layer. Accordingly, the algorithm may be organized in a hierarchical manner. This approach substantially reduces the computational burden on the processing unit (e.g. computer).

Embodiments of the present invention enable gradient data for a depth layer to be computed directly from a captured detector image without first requiring full tomosynthetic reconstruction of such depth layer. More specifically, a captured detector image is may be processed with a wavelet transform to result in gradient-based image data that may be processed to reconstruct (or compute) the gradient of a depth layer. The gradient that is computed for a depth layer directly from the captured detector image (e.g., from the wavelet transform of such detector image) may be used to perform auto-focusing operations. Further, such gradient may also be used for tomosynthetic reconstruction of the depth layer if such full reconstruction is desired (e.g., if the depth layer is determined by the auto-focusing process as including an in-focus view of a feature of the object under inspection that is of interest). Thus, certain embodiments of the present invention may be used for tomosynthetic reconstruction, irrespective of whether auto-focusing is to be performed. That is, a tomosynthetic reconstruction process is provided wherein the gradient of a depth layer is computed directly from a captured detector image (e.g., from the wavelet transform of such detector image), and such gradient may be further processed to tomosynthetically reconstruct a full image of the depth layer.

As described above, tomographic reconstruction has a long history of development and a lot of applications in many areas, like health monitoring, industrial vision, nondestructive inspection, airport security, etc. It is often desirable to provide a 3D tomographic technique that maintains high quality 3D reconstruction on one hand, and that provides high throughput of the 3D reconstruction on the other hand.

As described above, tomographic image processing of objects, such as solder joints on a printed circuit board, is utilized in automated inspection systems for quality control. For example, a solder joint on a printed circuit board may be imaged (e.g., by a radiographic imaging system), and such image may be processed by an automated inspection system to determine various parameters, such as length, width, curvature, relative opacity, and similar values of the solder joint. The various parameters determined for the solder joint may then be evaluated by the automated inspection system (or by a human inspector) to determine whether the solder joint is of acceptable quality.

As an example, the thickness of solder material (which is typically a combination of lead and tin) may be inspected by an automated inspection system through analysis of X-ray image(s) of the solder material. In an X-ray image of solder material, there is a relationship between the intensities comprising the X-ray image and the thickness of the solder material forming the X-ray image. Typically, the image intensity increases from values corresponding to lighter shades of gray (white) to values corresponding to darker shades of gray (black) as the thickness of the solder material increases. That is, the image of a thin section of solder will have a gray level that is less than the gray level of the image of a thicker section of solder. The image of the thin section will appear to be a lighter shade of gray than the image of the thicker section. This convention is typically used in electronic image representation of X-ray images, however, the opposite convention may also be used, i.e., where the image of a thin section of solder has a gray level that is greater than the gray level of the image of a thicker section of solder. The latter convention has traditionally been followed in film radiography where the X-ray images are recorded on X-ray film. Either convention may be implemented with embodiments of the present invention.

Embodiments of the present invention are preferably implemented in a digital tomography system that is operable to tomosynthetically reconstruct images from captured radiographic image data (pixels) of an object. Various such digital tomography imaging systems are well-known in the art, many of which may be used in conjunction with embodiments of the present invention, and thus example imaging systems are only briefly described herein so as not to detract attention away from the inventive system and method for performing auto-focus. As described further below, embodiments of the present invention provide an auto-focus technique that is particularly suited for use within a tomosynthesis system.

Example 3D tomography systems that have been proposed for use in industrial inspection systems and in which embodiments of the present invention may be implemented include those disclosed in U.S. Pat. No. 6,002,739 entitled "COMPUTED TOMOGRAPHY WITH ITERATIVE RECONSTRUCTION OF THIN CROSS-SECTIONAL PLANES" and U.S. Pat. No. 6,178,223 entitled "IMAGE RECONSTRUCTION METHOD AND APPARATUS," the disclosures of which are hereby incorporated herein by reference in their entirety. Of course, various other digital 3D tomography system configurations now known or later developed may be used, and embodiments of the present invention may be implemented with such systems to improve the efficiency thereof in the manner described further below. Embodiments of the present invention may be utilized in conjunction with any radiographic imaging device that is capable of capturing 2D image data (pixels) of an object under inspection, including without limitation well-known fan beam imaging systems and cone beam imaging systems. More specifically, as described further below, embodiments of the present invention may be utilized in conjunction with such a radiographic imaging device for efficiently reconstructing 3D image data (voxels) for the object under inspection from the captured pixel data.

Figure 1B:
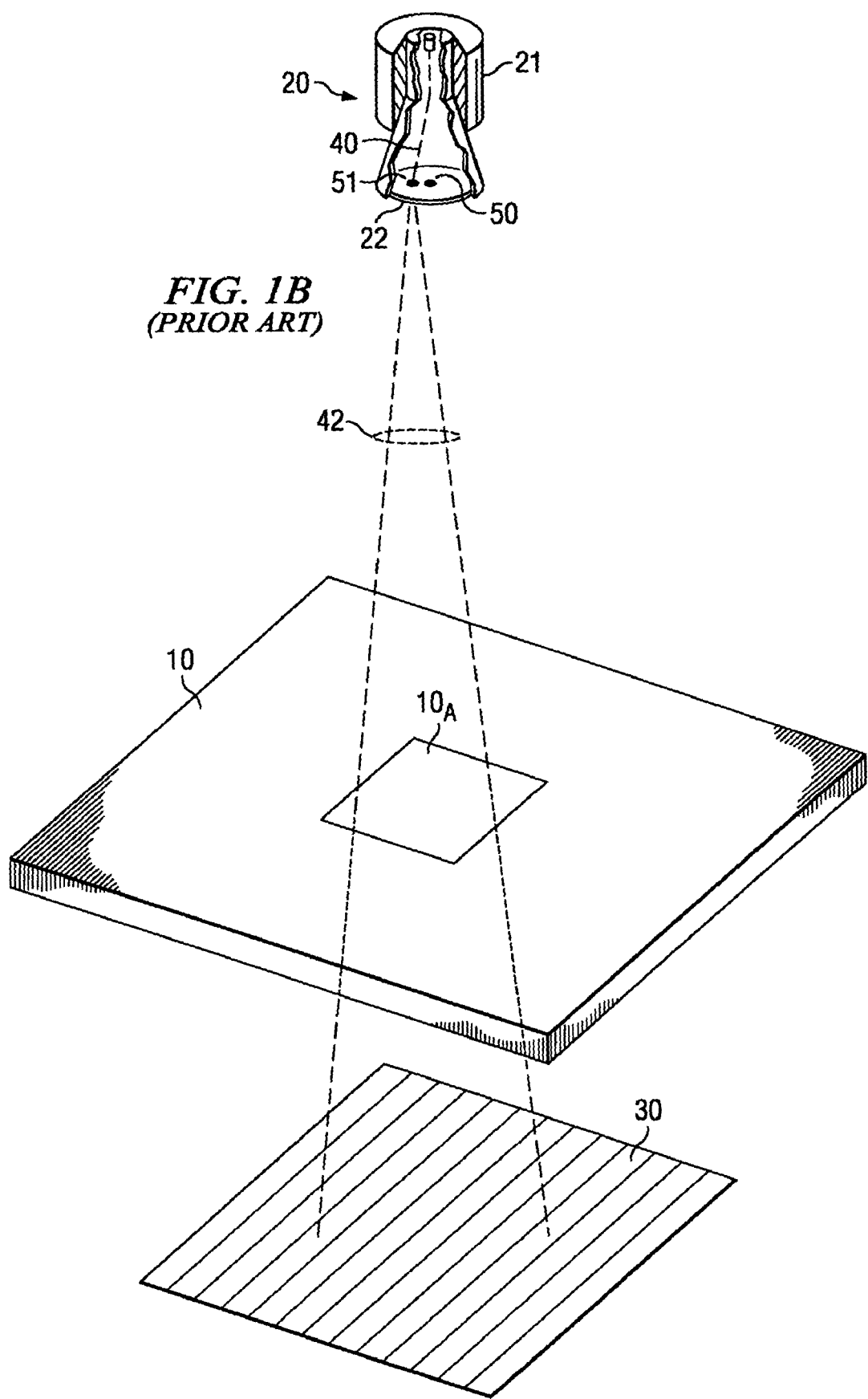

FIGS. 1A-1B show a schematic representation of an example digital tomosynthesis system geometry which may be used with embodiments of the present invention. More specifically, FIGS. 1A-1B show an example cone-beam tomography system. An X-ray source 20 emits X-rays toward an object 10 (e.g., a circuit board assembly) that is under inspection, and the X-rays that pass through object 10 are sensed by an array of sensors (or detectors) 30. To obtain multiple views of a region of object 10 (e.g., for reconstructing cross-sectional images of that region), one or more of X-ray source 20, object 10, and sensor array 30 may be effectively moved. For instance, FIG. 1A shows an example of a region $10_A$ of object 10 being imaged at a first angle of view, and FIG. 1B shows an example of such region $10_A$ of object 10 being imaged at a second angle of view. As described above, image data from multiple views of a region may be processed (e.g., with Back Projection or shift-and-add algorithms) to reconstruct cross-sectional images of the region.

In this example implementation, X-ray source 20 may include an electron beam source comprising a power supply (not shown) for operating X-ray source 20 at a desired voltage level to produce X-rays. Electron beam 40, which is generated within X-ray source 20 by a charged particle gun, is deflected over the source of a target assembly 22 (which may be a grounded anode) in a predetermined pattern (e.g., a scanning or stepping pattern). X-ray source 20 includes a mechanism to control the movement of electron beam 40 across target assembly 22, such as a deflection yoke 21 under the control of an electron beam pattern generator (not shown). One advantage provided by the example geometry of X-ray source 20 is that it allows X-rays to be projected at an object 10 from multiple angles without requiring physical relocation of the X-ray source 20. For instance, X-rays 41 may be generated by bombarding the surface of an X-ray tube with an electron beam 40, and by electronically deflecting the electron beam 40, the X-ray source 20 may be effectively moved. Thus, the X-ray source 20 and/or sensor array 30 may not actually move (but may instead be positionally-fixed) and instead the effect of their movement may be achieved through other techniques, such as by deflecting the X-ray tube's electron beam 40 (e.g., to achieve imaging of object 10 at various different angles of view).

In FIGS. 1A-1B, target assembly 22 is designed to emit X-rays forming a diverging beam 41 in FIG. 1A and forming diverging beam 42 in FIG. 1B that each directly intercept sensor array 30 (from different angles of view). In operation, electron beam 40 may first dwell at location 50 on target assembly 22, as shown in FIG. 1A. As the electron beam 40 strikes target assembly 22 at location 50, a diverging X-ray beam 41 is emitted. Electron beam 40 may then be directed to location 51 on target assembly 22, as shown in FIG. 1B. As the electron beam 40 strikes target assembly 22 at location 51, a diverging X-ray beam 42 is emitted, which enables image data to be acquired by sensor array 30 at a different angle of view from that of FIG. 1A. In certain embodiments, a collimator grid may be implemented to guide the X-ray beams 41 and 42, such as described in U.S. Pat. No. 6,178,223, in environments in which limiting the exposure of object 10 (or other objects present) to X-rays is desirable (e.g., when object 10 is a human subject, such as in medical applications).

Sensor array 30 may comprise a plurality of discrete detectors (referred to herein as "detector elements") arranged in an array. Each detector element includes a surface having a capture area for detecting X-rays, as is well-known in the art. Each detector element may be capable of independently measuring the amount of X-rays that strike it. When an object 10 is interposed between the X-ray source 20 and the sensor array 30, some of the X-rays in X-ray beam 41 (of FIG. 1A) will pass through a portion of object 10, and if not scattered or absorbed, will strike the detector elements that make up sensor array 30. The X-rays that strike any individual detector element comprise a portion of X-ray beam 41 that is referred to herein as an X-ray beam subpath.

Each detector element may comprise components for measuring the quantity of X-ray photons that strike the detector element and outputting a signal representative of that measurement. Alternatively, each detector element may include components for generating an electrical signal generally proportional to the total energy of the X-rays that strike the detector element. The magnitude of the generated electrical signals corresponds to the flux intensity of the X-rays from the appropriate X-ray beam subpath of X-ray beam 41. Each detector element may generate a pixel corresponding to the detected X-rays detected thereby. Utilizing a sensor array 30 that independently measures the X-rays which strike each detector element results in the generation of X-ray transmissiveness information that is proportional to the X-ray flux passing through object 10 along particular X-ray beam subpaths. The resulting intensity data can be used or manipulated to create a representation of object 10.

Of course, various other configurations of a digital radiographic imaging system operable to capture digital, radiographic images of an object 10 may be implemented with embodiments of the present invention, including without limitation that disclosed in U.S. Pat. No. 6,178,223. While a cone-beam radiographic imaging system, such as that of FIGS. 1A-1B, is used in conjunction with a preferred embodiment of the present invention, it should be recognized that the present invention is not limited to a specific configuration of a digital radiographic imaging system. Rather, any configuration of a digital radiographic imaging system operable to capture digital, radiographic image data (e.g., pixels) of an object 10 that are now known or later developed, including without limitation known cone-beam or fan-beam imaging systems, may be implemented with embodiments of the present invention. That is, various configurations now known or later developed for capturing digital, radiographic images of an object 10 may be used in conjunction with the autofocus and tomosynthetic image reconstruction processes described hereafter for efficiently reconstructing, from the captured radiographic image data (pixels) cross-sectional images for desired layer(s) of object 10 (or regions thereof).

Conventional 3D digital tomography approximates an object by discrete volume elements, called voxels. "Voxels" (or "volume pixels") are well known in the art of image processing, and are commonly used in 3D imaging. In general, a voxel is the smallest distinguishable box-shaped part of a three-dimensional image.

For better understanding of certain principals commonly utilized in 3D tomography and which may be utilized in certain embodiments of the present invention described herein below, aspects of conventional image processing techniques are described in conjunction with FIGS. 2A-2C. Just as embodiments of the present invention are not limited to the example radiographic imaging system configuration described in conjunction with FIGS. 1A-1B, embodiments of the present invention are not intended to be limited in any way by the general image processing principals described in conjunction with FIGS. 2A-2C. Rather, image processing principals, such as use of voxels, are briefly described in conjunction with FIGS. 2A-2C to aid the understanding of the reader to the extent that such principals are described herein as being used in embodiments of the present invention.

Figure 2A:
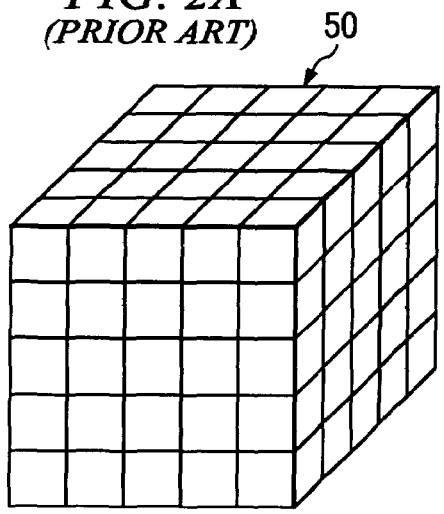
FIG. 2A shows a cubical object that has been divided into 125 (5×5×5) identically sized cubic voxels.
Figure 2B:
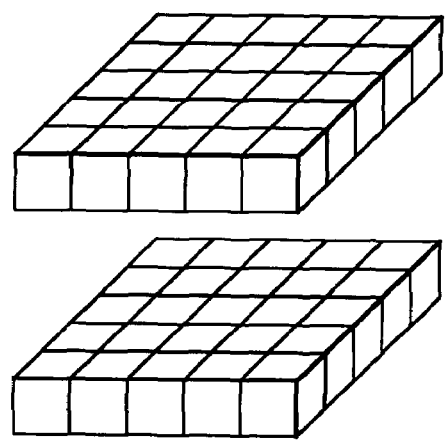
FIG. 2B shows two layers of voxels for the object of FIG. 2A.

FIG. 2A illustrates a cubical object 50 that has been divided into 125 (5×5×5) identically sized cubic voxels. For 3D imaging of object 50, the density (or absorption coefficient, or material thickness) of each of the 125 voxels is reconstructed from the data represented in multiple views (at different angles of view) of object 50 as detected by an array of sensors such as array 30 in FIGS. 1A-1B. That is, tomosythesis techniques may be used to reconstruct the voxels from the detector data detected (or captured) by array 30.

For many applications, a complete 3D image is not necessary. For example, for inspection of a double-sided circuit board (such as that shown in FIG. 4), a few image planes or "cross-sections" (such as image planes 410 and 412 in FIG. 4) may be sufficient to determine solder joint quality. For instance, in certain applications only a portion of the layers of an object under inspection may be of interest. Thus, FIG. 2B shows two layers of voxels for the object 50 of FIG. 2A, wherein the two layers shown may be the layers of interest for a given application.

Figure 2C:
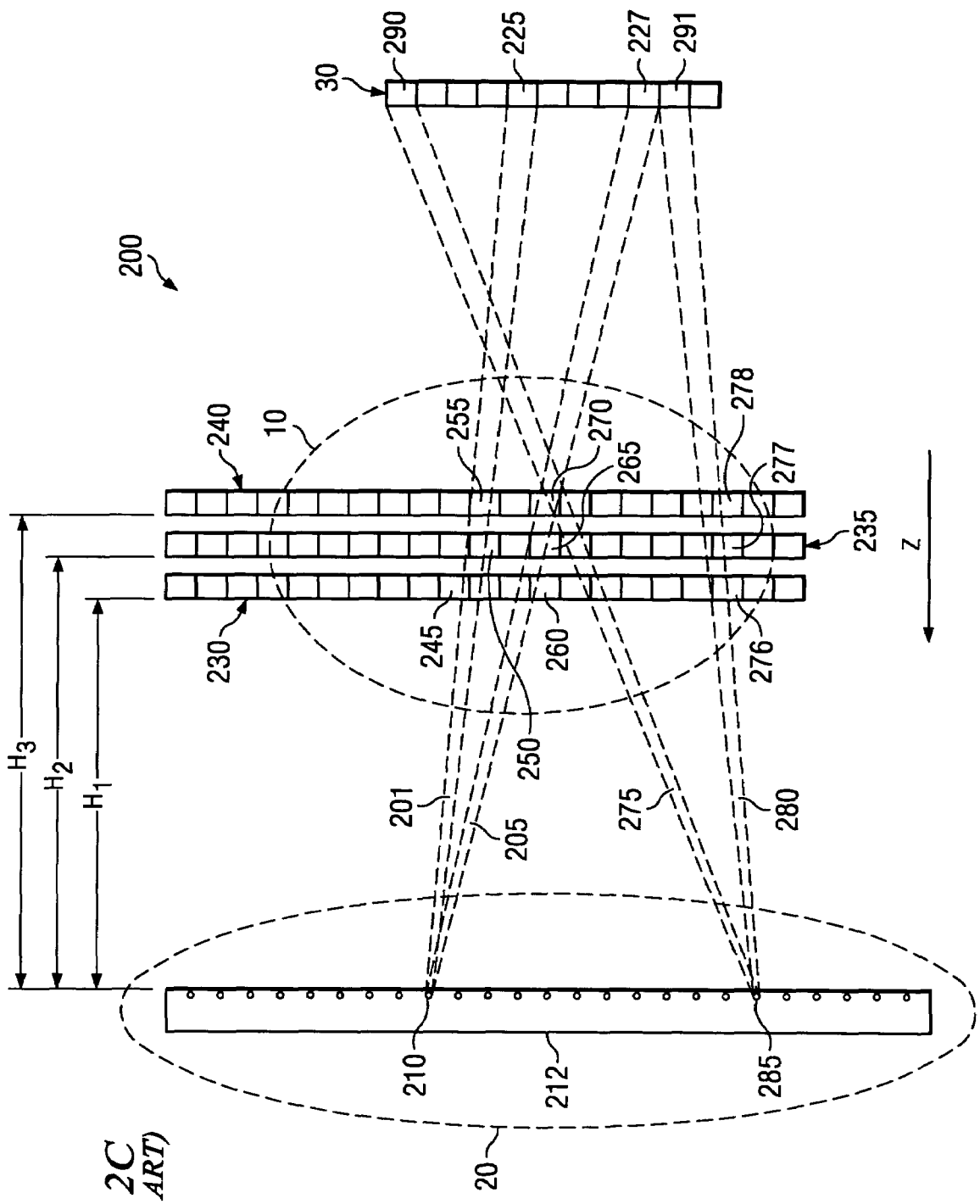
FIG. 2C shows an example radiographic imaging system that may be used for capturing 2D radiographic images of an object, which may be processed in accordance with embodiments of the present invention.

Referring to FIG. 2C, an example radiographic imaging system 200, such as that described more fully in U.S. Pat. No. 6,178,223, that may be used for capturing radiographic images of object 10 is shown. In this example configuration of a radiographic imaging system, source 20 includes a collimator grid 212 that is capable of serially directing a plurality of X-ray beams (which may comprise a plurality of X-ray beam subpaths, as described hereafter) to object 10 at various different angles. That is, an X-ray beam is first directed to object 10 at a first angle, and then an X-ray beam is directed to object 10 at a second angle, and so on, to obtain image data for object 10 at a plurality of different angles of view. While collimator grid 212 is used in the example system 200 of FIG. 2C to direct X-ray beams to object 10 at various different angles for capturing sufficient data for reconstructing various depth layers of object 10, it should be recognized that various other techniques now known or later discovered for simultaneously or serially generating X-ray beams that are directed to object 10 at various different angles may be used in other configurations.

As shown in this example, a first X-ray beam subpath 201 and second X-ray beam subpath 205 are ones of many X-ray beam subpaths emanating from a first aperture 210 of collimator grid 212. The remaining X-ray beam subpaths are not shown for the sake of clarity and explanation. Some of the X-rays that travel along first X-ray beam subpath 201 and second X-ray beam subpath 205 pass through object 10 and strike detectors 225 and 227, respectively, of multi-detector array 30. It will be recognized that the information provided to detector 225 by X-rays traveling along first X-ray beam subpath 201 does not correspond to any single point within object 10; rather the path of the first X-ray beam subpath 201 as it passes through the object 10 forms a line which intersects first slice (or "cross-section" or "depth layer") 230, second slice, 235, and third slice 240. Particularly, X-rays traveling along first X-ray beam subpath 201 pass through the volume which is completely or partially coincident with first voxel 245 (of depth layer 230), second voxel 250 (of depth layer 235), and third voxel 255 (of depth layer 240).

The information obtained by detector 225 from X-ray beam subpath 201 may contribute to reconstruction of a first voxel 245 in a reconstructed cross-sectional image corresponding to depth layer 230, to reconstruction of a second voxel 250 in a reconstructed cross-sectional image corresponding to depth layer 235, and to reconstruction of a third voxel 255 in a reconstructed cross-sectional image corresponding to depth layer 240. Thus, pixel data output from detector 225 of sensor 30 generally contributes to reconstruction of voxels of a plurality of different cross-sections (or depth layers) of object 10. Such pixel data is received by an image reconstruction processor, which may process the pixel data in the manner described more fully herein below to perform auto-focusing and to reconstruct one or more of the plurality of different cross-sections.

With respect to second X-ray beam subpath 205, the information provided by detector 227 may contribute to reconstruction of a fourth voxel 260 in a reconstructed cross-sectional image corresponding to depth layer 230, to reconstruction of a fifth voxel 465 in a reconstructed cross-sectional image corresponding to depth layer 235, and to reconstruction of a sixth voxel 270 in a reconstructed cross-sectional image corresponding to depth layer 240.

A third X-ray beam subpath 275 and fourth X-ray beam subpath 280 are two of many X-ray beam subpaths emanating from a second aperture 285. The remaining X-ray beam subpaths emanating from second aperture 285 are not shown for the sake of clarity and explanation. Some of the X-rays that travel along X-ray beam subpath 275 and X-ray beam subpath 280 pass through object 10 and strike detectors 290 and 291, respectively. As described above with subpaths 201 and 205, the intensity information provided to detector 290 by X-rays traveling along third X-ray beam subpath 275 does not correspond to any single point within object 10; rather the intensity information is an aggregation of information for a volume that intersects all plane/slices between collimator grid 212 of source 20 and multi-detector array 30, including the plane/slices containing voxel 270. Likewise, the intensity information provided to detector 291 by X-rays traveling along fourth X-ray beam subpath 280 does not correspond to any single point within object 10; rather the intensity information is an aggregation of information for a volume that intersects all plane/slices between collimator grid 212 of source 20 and multi-detector array 30, including the plane/slices containing voxels 276, 277, and 278.

Pixel data corresponding to the intensity detected by sensor 30 may be output by radiographic imaging system 200 to an auto-focus processor or to an image reconstruction processor that may be operable to perform auto-focusing, such as that described more fully below. As described below, the auto-focus processor (or the image reconstruction processor) may be operable to determine the layer(s) of focus. That is, an auto-focus technique may be implemented to determine those layer(s) that when reconstructed via tomosynthetic reconstruction using the detector data output by sensor array 30 is/are in focus. In certain embodiments, the layer(s) in focus may be reconstructed via an image reconstruction processor. Image reconstruction processors are known in the art that are operable to process the received pixel data by, for example, combining or summing the intensity for a voxel from all of the detectors that detect X-rays traveling along X-ray beam subpaths that are completely or partially coincident with that particular voxel and have been assigned to that voxel for the purpose of reconstruction. For example, intensity data collected by detector 227 from X-ray beam subpath 205 in a first pixel output thereby and intensity data collected by detector 290 from X-ray beam subpath 275 in a second pixel output thereby may be used in reconstructing sixth voxel 270 (as both X-ray beam subpaths 205 and 275 intersect with sixth voxel 270). As described further below, an auto-focus technique is provided that enables reduced computational load by determining layer(s) that are in focus without requiring that all layers be reconstructed to make such determination.

The radiographic imaging geometry and apparatus shown and described with reference to FIGS. 1A-1B and 2C are typical of that which may be used in conjunction with embodiments of the present invention. However, specific details of these systems are not critical to the practice of the present invention, which addresses auto-focusing techniques for tomosynthetic reconstruction of images. For example, the specific details of the X-ray source, detector, positioning mechanism(s) for positioning the object under inspection, control system (e.g., computer) for controlling the operation of the imaging system, etc. may vary considerably from system to system. Embodiments of the present invention are generally applicable to any type of computer aided tomosynthesis system for performing auto-focusing.

FIGS. 3A-3D show example cross-sectional images that may be produced by a reconstruction process for a sample object 10. For illustrative purposes, object 10 shown in FIG. 3A includes test patterns in the shape of an arrow 81, a circle 82, and a cross 83 embedded within the object 10. As shown, in this example, arrow 81 spans depth layers 60A-60E of object 10, and is followed by 50 "empty" layers 61. Circle 82 spans depth layers 62A-62G of object 10. Below circle 82 are 100 empty layers 63. Cross 83 spans depth layers 64A-64D and is followed by 50 empty layers 65.

Figure 3C:
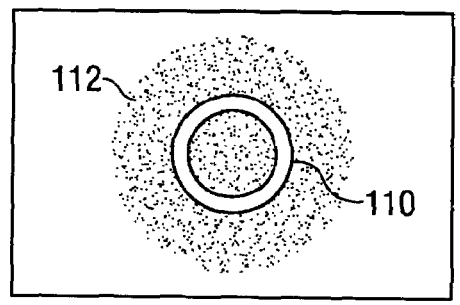
FIGS. 3B-3D show example cross-sectional images that may be tomosynthetically reconstructed for the sample object of FIG. 3A.
Figure 3B:
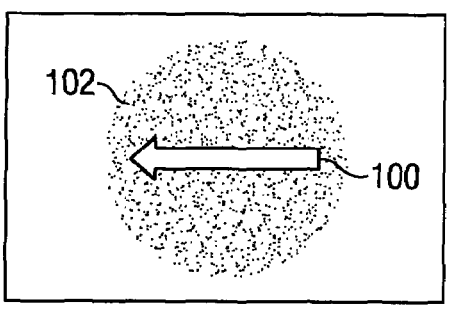

FIG. 3B shows a sample cross-sectional image (or "tomograph") of a depth layer comprising arrow 81 (e.g., depth layer 60C) of object 10 that may be reconstructed by an image reconstruction processor (e.g., via tomosynthesis). The image 100 of arrow 81 is in sharp focus, while the images of other features within the object 10, such as the circle 82 and cross 83 may form a blurred region 102 which does not greatly obscure the arrow image 100. Preferably, blurred region 102 and/or its effects on the arrow image 100 is minimized in the reconstruction process to provide a high-quality image of the cross-section.

Similarly, FIG. 3C shows a sample cross-sectional image (or "tomograph") of a depth layer comprising circle 82 (e.g., depth layer 62D) of object 10 that may be reconstructed by an image reconstruction processor (e.g., via tomosynthesis). The image 110 of circle 82 is in sharp focus, while the images of other features within the object 10, such as the arrow 81 and cross 83 may form a blurred region 112 which does not greatly obscure the circle image 110. Again, preferably blurred region 112 and/or its effects on the circle image 110 is minimized in the reconstruction process to provide a high-quality image of the cross-section.

Figure 3D:
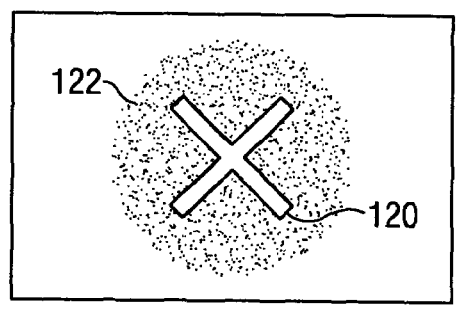

FIG. 3D shows a sample cross-sectional image (or "tomograph") of a depth layer comprising cross 83 (e.g., depth layer 64C) of object 10 that may be reconstructed by an image reconstruction processor (e.g., via tomosynthesis). The image 120 of cross 83 is in sharp focus, while the images of other features within the object 10, such as the arrow 81 and circle 82 may form a blurred region 122 which does not greatly obscure the cross image 120. Again, preferably blurred region 122 and/or its effects on the cross image 120 is minimized in the reconstruction process to provide a high-quality image of the cross-section.

Figure 3A:
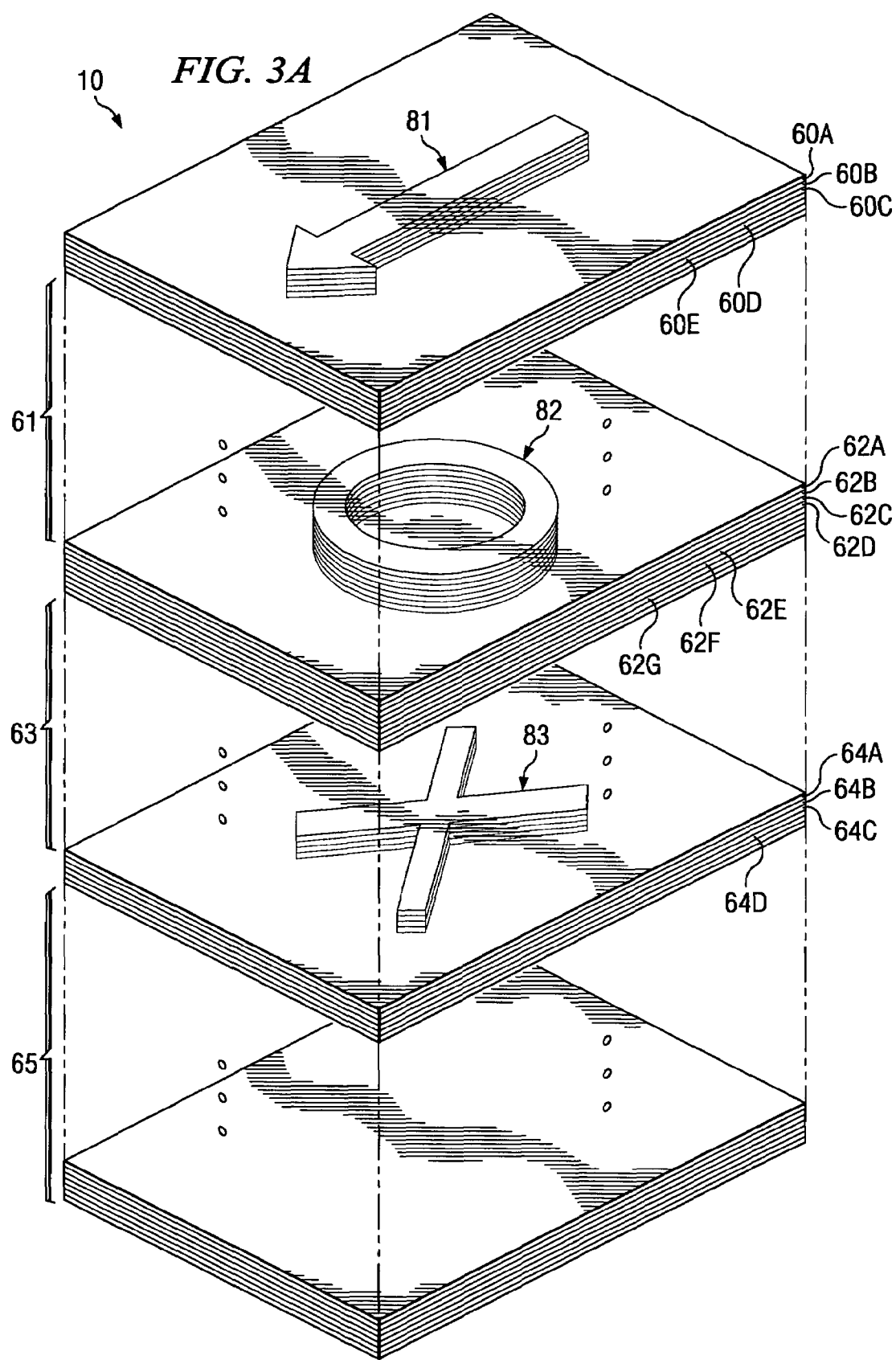
FIG. 3A shows example depth layers of an object under inspection.
Figure 4:
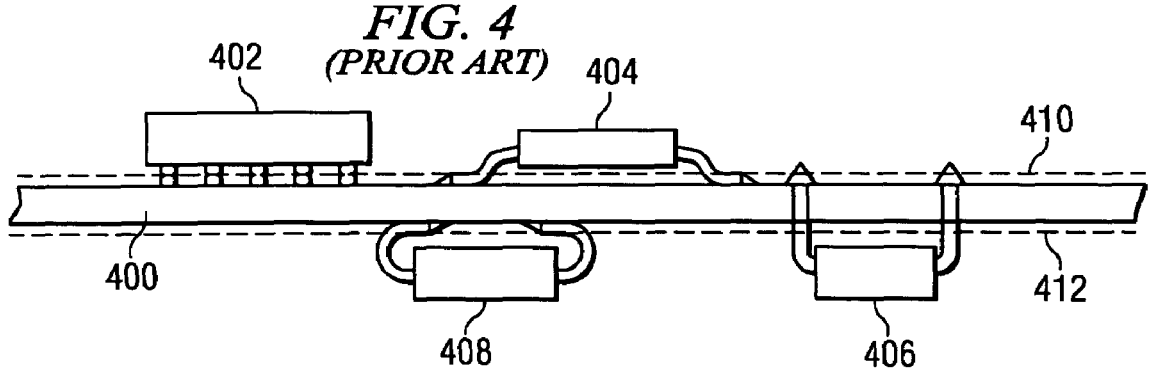
FIG. 4 shows an example printed circuit board assembly that may be inspected in accordance with embodiments of the present invention.

While FIGS. 3A-3D show an example object 10 having depth layers 60A-E, 61, 62A-G, 63, 64A-D, and 65, it should be recognized that object 10 is intended as a generic example to illustrate the concept of reconstructing various depth layers of an object as cross-sectional images. In practice, various other types of objects having any number of depth layers may be inspected, and any number of their depth layers may be reconstructed as cross-sectional images. For example, embodiments of the present invention may be implemented with an automated inspection system for inspecting solder joints on a printed circuit board. FIG. 4, described further below, depicts an example printed circuit board assembly that may have various depth layers thereof reconstructed as cross-sectional images by an image reconstruction processor in order to inspect the printed circuit board assembly.

Further, in many applications, only certain one(s) of the depth layers 60A-E, 61, 62A-G, 63, 64A-D, and 65 and/or certain one(s) of features 81-83 may be of interest. As described above, the location of those layers of interest (e.g., a layer that comprises a desired feature, such as arrow 81, and that is in focus) may be determined after acquisition of the image data using an appropriate analysis of image layers. More specifically, an auto-focus algorithm may be utilized by a processing unit to select layer(s) that maximize some constraint, such as image sharpness. For example, arrow 81 may be of interest for a given application (e.g., for inspection of such arrow 81), in which case an auto-focus algorithm may be utilized to identify a depth layer that comprises arrow 81 and maximizes some constraint, such as image sharpness. Thus, for instance, an auto-focus algorithm may analyze various depth layers around and/or that include arrow 81 to determine a depth layer that includes arrow 81 and that is most in-focus (e.g., has the best image sharpness). The location (in free space) of a depth layer that includes arrow 81 may not be precisely known before capturing radiographic images of object 10, and as mentioned above, auto-focusing may be performed using the captured radiographic images to determine a depth layer that is most in focus (e.g., that has the maximum sharpness). For instance, assuming it is desired to have an in-focus reconstructed image of a depth layer of object 10 that includes arrow 81, many depth layers in a region of object 10 (e.g., a region spanning 30 or more depth layers) may be evaluated by an auto-focus algorithm to determine an appropriate depth layer that provides an in-focus image of arrow 81. Depending on the specific arrangement/positioning of object 10 within the imaging system, the location of the exact depth layer that provides such an in-focus image of arrow 81 may vary, and thus auto-focusing identifies an in-focus image of a feature of interest, as is well-known in the art.

As described further below in conjunction with FIG. 5, traditional auto-focus techniques require that all layers of the object (or at least all potential layers that may comprise a feature of interest, such as arrow 81) first be reconstructed as full images and then those reconstructed images are analyzed to determine the layer(s) of interest (e.g., the layer that comprises a feature of interest, such as arrow 81, in-focus). For instance, a range of depth layers are predetermined as forming a region of depth layers (e.g., 30 or more depth layers in many cases) in which an in-focus depth layer comprising a feature of interest (e.g., arrow 81) resides. In the example of FIG. 3A, when using a traditional auto-focus algorithm to focus on a layer that comprises arrow 81, layers 60A-60E are all tomosynthetically reconstructed (and several other layers, such as all or a portion of the 50 empty layers 61 may also be tomosynthetically reconstructed) from captured radiographic images of object 10, and those reconstructed layers are analyzed by the auto-focus algorithm to determine a reconstructed layer that includes a desired feature (e.g., arrow 81) and maximizes some constraint, such as image sharpness. Thus, the one of the tomosynthetically reconstructed layers having the maximum image sharpness, for example, is identified by the auto-focus algorithm. As described further hereafter, such traditional auto-focusing technique is compute intensive as it requires full tomosynthetic reconstruction of each potential layer in which a feature of interest may reside (which may be 30 or more layers in many instances), which is undesirable for high-speed applications.

FIG. 4 provides a concrete example of an object that may be inspected in accordance with embodiments of the present invention. Of course, embodiments of the present invention are not intended to be limited solely in application to auto-focusing and reconstructing cross-sectional images of a circuit board, but may instead be utilized in many other applications, including without limitation inspection of various other types of products in a manufacturing environment for quality control, use in automated inspection systems for inspecting objects for contraband contained therein (e.g., security systems for inspecting passenger luggage at an airport or other transportation facility), and/or use in various medical applications. Various other applications of the auto-focus and image reconstruction process of embodiments of the present invention will be recognized by those of ordinary skill in the art.

In FIG. 4, a double-sided printed circuit board 400 has multiple components soldered to each of two exterior surfaces. Components 402 and 404 are mounted onto a first surface. Component 408 is mounted onto a second surface that is opposite the first surface. Component 406 is a through-hole component mounted onto the second surface, but with leads that pass through both surfaces of board 400. Typically, the electrical connections coupling components 402, 404, 406, and 408 to board 400 are formed of solder. However, various other techniques for making the electrical connections are well known in the art and even though example embodiments of the present invention will be described herein in terms of solder joints, it should be understood that other types of electrical connections, including but not limited to conductive epoxy, mechanical, tungsten and eutectic bonds, may be inspected utilizing embodiments of the invention.

In this example, component 402 has a ball-grid array (BGA) of solder joints. Component 404 illustrates a gull-wing surface mount device. Component 408 is a J-lead surface mount device. One plane (or depth layer), depicted dashed line 410, just off the first surface of circuit board 400 passes through the leads and solder fillets of components 402, 404, and 406. Another plane (or depth layer), depicted by dashed line 412, just off the second surface of circuit board 400 passes through the leads and solder fillets of components 406 and 408. It should be understood that while two example depth layers (410 and 412) are specified in this example, in other examples any number of depth layers of circuit board 400 may be examined. Further, while various types of solder joints (e.g., surface mounts and in-board joints) are shown in this example as being included within a common depth layer, such as the various joints of components 402, 404, and 406 falling within depth layer 410, it should be understood that in some implementations different types of solder joints may actually fall within different depth layers of the circuit board (which may increase the number of depth layers being processed by an inspection system). Only one depth layer corresponding to each side of circuit board 400 is shown in this example for simplicity and ease of illustration, but in actual application a plurality of depth layers may be of interest on each side of circuit board 400. While it may be useful in certain applications to have a 3D image of each solder joint, generally image planes 410 and 412 provide sufficient information to determine that each component lead is present and/or provide useful information for inspection of the various solder joints (e.g., inspection of the quality of such solder joints).

According to various embodiments of the present invention, 2D radiographic image data (pixels) of an object under inspection (e.g., circuit board 400) may be captured by a radiographic imaging system, such as those described above, and input to an image reconstruction processor. The image reconstruction processor may process the captured pixel data utilizing an auto-focus algorithm, such as described further below, to identify the layer(s) of interest. Further, the image reconstruction processor may process the captured pixel data to construct 3D (voxel) image data of the identified layer(s) of the object that are of interest, such as one or more of the example cross-sectional images described above in conjunction with FIGS. 3A-3D. Once produced, the cross-sectional images of the solder joints of board 400 (or other portions of an object under inspection) may, in certain implementations, be automatically evaluated by the automated inspection system to determine their quality and physical characteristics, including, for example, solder thickness. Based on an evaluation by the inspection system, a report of the solder joint quality and physical characteristics and/or the reconstructed cross-sectional images of the solder joints may presented to the user.

It is to be understood that the term "image" (or "image data"), as used herein, is not limited to formats which may be viewed visually, but may also include digital representations that may be acquired, stored, and analyzed by the computer. Thus, the term "image" (or "image data"), as used herein, is not limited to a viewable image, but is intended to also encompass computer data that represents the image and/or that may be processed by a computer for displaying a viewable image. For instance, in certain embodiments, the reconstructed cross-sectional images may be displayed to a user for inspection by such user in addition to or instead of automated inspection by the computer. In other embodiments, the reconstructed images may not be displayed to a user, but instead the reconstructed image data may be autonomously analyzed by the computer for quality control.

As described above, tomosynthetic reconstruction techniques are known in the art, and such techniques generally require many images acquired at several different perspectives (or angles of view). Such acquired images may be processed to reconstruct various different layers of an object under inspection. However, as also mentioned above, in many applications only a portion of the layers may be of interest (e.g., only a portion of the layers may include an in-focus image of a feature of interest). Thus, it becomes desirable to identify those layer(s) that are of interest. The specific position in space of those layer(s) of interest may be unknown at the time of acquiring the image data. For instance, with reference again to FIG. 2C, the specific height $H_1$ of layer 230, the specific height $H_2$ of layer 235, and the specific height $H_3$ of layer 240 may be unknown at the time of capturing the image data by detector 30. Assume, for instance, that layer 240 is of interest, an auto-focus technique may be used to determine the position (e.g., the height $H_3$) at which such layer 240 resides in space.

Traditionally, a laser mapping system may be utilized to actually map out the height along the "Z" axis of the object under inspection in all locations to be inspected. For instance, in an inspection system for inspecting a circuit board, a laser mapping system may be employed to map out the vertical distance between the source 20 and the surface of the board.

As an example, in an imaging system that uses laminography for image reconstruction, such as the 5DX X-ray imaging system available from Agilent Technologies, an appropriate locating or measurement means is typically used to locate the vertical height of the focal plane of interest (e.g., the height $H_3$ of layer 240 that is of interest in the above example). For instance, in the 5DX system a laser-based surface mapping system is used to map the height of a circuit board under inspection. This focusing step typically must be done in advance, and separately from, the actual reconstruction and inspection process. That is, the laser mapping is traditionally performed before imaging an object in an attempt to identify the positioning of the object relative to the source, detector, etc. within the imaging system.

The laser mapping technique for focusing on a layer of interest is disadvantageous for several reasons. One disadvantage is that implementing the laser mapping system increases the cost associated with the image processing system. That is, the laser mapping system is undesirably expensive. Another disadvantage is that the laser mapping technique provides limited measurement accuracy. For instance, the laser mapping technique provides a mapping of the surface of a circuit board (or other object) under inspection. If, rather than residing at the surface of a circuit board, the layer of interest actually resides at a different position (e.g., within the interior of the circuit board), then knowledge of the circuit board layout may be used to estimate the location of the layer of interest. However, such mapping technique provides limited accuracy. Further, the laser mapping system is undesirably slow in focusing on a layer of interest, thereby extending the overall time required for reconstructing an image of the layer of interest, which may be unacceptable for many high-speed applications.

As an alternative, tomosynthetic reconstruction allows for the elimination of the laser-mapping step, if an auto-focusing algorithm is used to find the desired layer(s) of interest (i.e., to find a layer of a feature of interest that is "in focus"). Unfortunately, traditional auto-focusing algorithms may be computationally prohibitive. That is, as described above, auto-focusing algorithms enable a desired (or "in focus") layer to be identified after acquisition of the radiographic image data (pixels), through analysis of such acquired image data. For instance, the in focus layer may be identified as one in which some constraint, such as image sharpness, of the desired layer is maximized. However, the traditional auto-focus techniques process the acquired image data (in order to identify a layer that is in focus) in a manner that is computationally burdensome, as described further below. Thus, traditional auto-focusing processes may require too much time and/or too many computational resources to be utilized in certain high-speed applications.

With traditional auto-focus algorithms, all layers of an object under inspection (or at least all layers that may potentially include an in focus image of a feature of interest) are reconstructed into full images, and then the reconstructed full images are analyzed to determine the layer(s) of interest (i.e., the layer(s) that include a feature of interest and are in focus). For instance, as described with the example of FIG. 3A above, all layers that may potentially include a feature of interest (e.g., arrow 81) may be tomosynthetically reconstructed, and the sharpest layer may be selected by the auto-focus technique. Fully reconstructing all layers that may potentially include a feature of interest (which often entails fully reconstructing 30 or more layers) is computationally burdensome.

Figure 5:
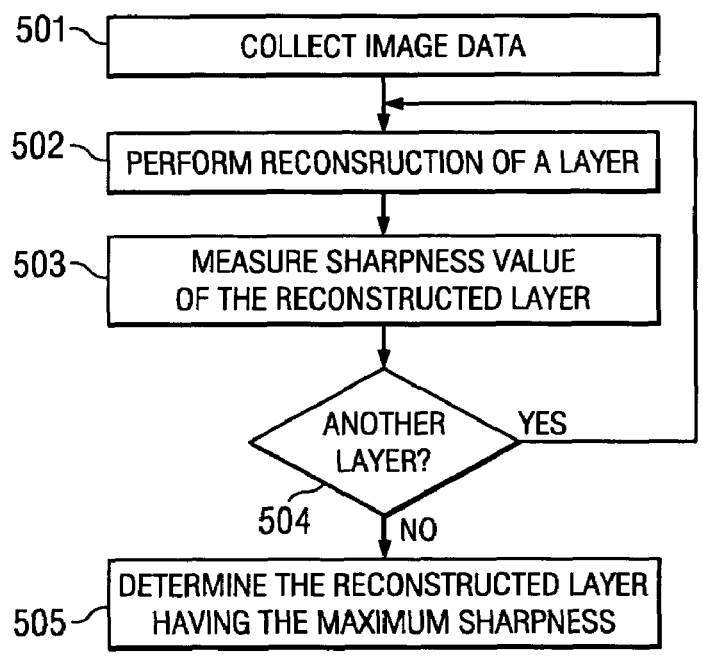
FIG. 5 shows an example operational flow of a traditional auto-focusing technique.

An example of a traditional auto-focusing technique is shown in FIG. 5. That is, FIG. 5 shows an example operational flow of a traditional auto-focusing technique. In operational block 501, image data (e.g., detector data) is captured by an imaging system, such as with the example system of FIG. 2C. In operational block 502, the captured image data is processed to reconstruct a full image (or high-resolution image) of a layer in accordance with a reconstruction process (e.g., tomosynthesis). In block 503, a constraint (or characteristic) of the reconstructed layer, such as its sharpness, is measured. In block 504, the auto-focus process determines whether another layer exists in the object under inspection (or another layer in which a feature of interest may potentially reside). If another layer is to be reconstructed (e.g., may potentially include an image of a feature of interest), then operation returns to block 502. In many cases, 30 or more layers may be fully reconstructed, and their respective sharpness values (and/or other characteristic) may be measured. Once it is determined at block 504 that all of the layers of the object have been reconstructed (or at least all of the layers that may potentially include a feature that is of interest), operation advances to block 505 whereat the reconstructed layer having the maximum sharpness (and/or other characteristic) is determined as the desired layer (or layer of focus).

A more specific example of an existing auto-focus technique performs the following steps:
1. reconstruction of a specific layer using tomosynthesis;
2. computation of the horizontal and vertical gradients of the image of the reconstructed layer, as may be computed using various digital filtering schemes, such as the well-known Sobel gradient filter;
3. combining horizontal and vertical gradients using a specified norm, such as the 1-norm (max norm), or 2-norm (mean-square norm);
4. computation of the standard deviation of the result, which serves as a measure of sharpness of the reconstructed layer; and
5. repeating the above process on multiple layers, and identifying the maximum sharpness value of all layers to determine the layer of interest.

A disadvantage of the traditional auto-focusing approach is that multiple layers, perhaps 20 or 30, must be tomosynthetically reconstructed in order to find the sharpest one. In many applications, such as in an industrial grade inspection system, it is desirable to have the image reconstruction be performed very quickly (e.g., in real time), which places a tremendous burden on the computational engine. The number of arithmetic operations, also referred to as the "computational cost," of the above-described auto-focus algorithm is approximately $((2P+3)MN)L$, where P is the number of projection (or detector) images, M×N is the number of pixels in the reconstructed image, and L is the number of layers reconstructed. Thus, for performing auto-focusing using the above algorithm in which 16 projection images are used for reconstructing a layer (e.g., 16 images at different angles of view), the computational cost is estimated as $(35MN)L$. If reconstructed images are of size M×N=10 Megapixels, and if 30 layers are reconstructed from 16 projection images, then the total cost is about 10.5 billion arithmetic operations. The amount of time available for performing these computations in many high-speed applications may be less than a few seconds.

Another disadvantage of the above-described auto-focus algorithm is that the efficacy of the gradient filter may vary considerably from feature to feature. In particular, the sharpness of different features may be more accurately represented using filters of different sizes. Increasing the size of the filter may improve the efficacy of the operation in certain cases, but at the expense of even greater computational cost.

Many examples of methods designed to improve the quality and/or speed of tomographic image reconstruction have been proposed in the existing art. Recently, multiresolution methods based on hierarchical functions, especially wavelets have been the focus of much research, see e.g., I. Daubechies, "Orthonormal Bases of Compactly Supported Wavelets", Comm. Pure and Appl. Math, Vol. 41, pp. 909-996, 1988; S. G. Mallat, "A Theory for Multiresolution Signal Decomposition: the Wavelet Representation", IEEE Transactions on Pattern Analysis and Machine Intelligence, Vol. 11, Issue 7, pp. 674-693, 1989; and Beylkin, et al., "Fast Wavelet Transforms and Numerical Algorithms I", Comm. Pure and Appl. Math., Vol. 44, pp. 141-183, 1991, the disclosures of which are hereby incorporated herein by reference. In the area of image reconstruction, the application of wavelets falls generally into a few categories, which are discussed further below.

A first category of wavelet application is in tomography, primarily in the use of the so-called Filtered Back-Projection algorithm (FBP) in the medical industry. Here, the emphasis is on reducing the patient's exposure to X-band radiation by constructing a "region of interest" based method that requires fewer X-ray projections to be taken (see e.g., Rashid-Farrokhi, et al., "Wavelet-Based Multiresolution Local Tomography", IEEE Transactions on Image Processing, Vol. 6, Issue 10, pp. 1412-1430, 1997; Olson, et al., "Wavelet Localization of the Radon Transform", IEEE Transactions on Signal Processing, Vol. 42, Issue 8, pp. 2055-2067, 1994; DeStefano et al., "Wavelet Localization of the Radon Transform in Even Dimensions", Time-Frequency and Time-Scale Analysis, 1992, Proceedings of the IEEE-SP International Symposium, pp. 137-140, 4-6 Oct. 1999; Warrick, et al., "A Wavelet Localized Radon Transform", Proceedings of the SPIE—The International Society for Optical Engineering, Vol. 2569, Part 2, pp. 632-643, 1995; Warrick, et al., "A Wavelet Localized Radon Transform Based Detector for a Signal with Unknown Parameters", Signals, Systems and Computers, Vol. 2, pp. 860-864, Oct. 30, 1995-Nov. 2, 1995; Sahiner, et al., "On the Use of Wavelets in Inverting the Radon Transform", Nuclear Science Symposium and Medical Imaging Conference, 1992, IEEE, Vol. 2, pp. 1129-1131, 25-31 Oct. 1992; A. E. Yagle, "Region-of-Interest Tomography Using the Wavelet Transform and Angular Harmonics", Image Processing, Proceedings, Vol 2, pp. 461-463, 23-26 Oct. 1995; and U.S. Pat. Nos. 5,953,388 and 5,841,890). These methods are not particularly useful in industrial applications, however, since there is little motivation to reduce dose levels. Additionally, such methods are not particularly desirable for many high-speed applications because full tomographic reconstruction is typically too computationally costly in a high-speed (e.g., real-time) computing environment.

Besides the FBP algorithm, the Conjugate-Gradient method may be used for tomography, and wavelets have been used here as well, primarily as a means of making the computations more stable, see e.g., David L. Donoho, "Nonlinear Solution of Linear Inverse Problems by Wavelet-Vaguelette Decomposition", Applied and Computational Harmonic Analysis, Vol. 2, Issue 2, pp. 101-126, April 1995; T. Olson, "Limited Angle Tomography Via Multiresolution Analysis and Oversampling", Time-Frequency and Time-Scale Analysis, 1992, Proceedings of the IEEE-SP International Symposium, pp. 215-218, 4-6 Oct. 1992; Sahiner, et al., "Limited Angle Tomography Using Wavelets", Nuclear Science Symposium and Medical Imaging Conference, 1993, Vol. 3, pp. 1912-1916, 31 Oct. 1993-6 Nov. 1993; W. Zhu, et al., "A Wavelet-Based Multiresolution Regularized Least Squares Reconstruction Approach for Optical Tomography", IEEE Transactions on Medical Imaging, Vol. 16, Issue 2, pp. 210-217, April 1997; M. Bhatia, et al., "Wavelet Based Methods for Multiscale Tomographic Reconstruction", Engineering in Medicine and Biology Society, Proceedings, Vol. 1, pp. A2-A3, 3-6 Nov. 1994; Natha, et al., "Wavelet Based compression and Denoising of Optical Tomography Data", Optics Communications, Vol. 167, Issues 1-6, pp. 37-46, 15 Aug. 1999; and U.S. Pat. No. 6,351,548.

Another category of wavelet application is in the area of feature extraction and de-noising. As is well known in the art, wavelets provide an excellent framework for distinguishing between signal and noise. Reconstructed image quality may be improved by using de-noising techniques comprising applying a wavelet transform and using various analysis methods to modify the data, see e.g., Bronnikov, et al., "Wavelet-Based Image Enhancement in X-ray Imaging and Tomography", Applied Optic, Vol. 37, Issue 20, pp. 4437-4448, 1998; M. D. Harpen, "A Computer Simulation of Wavelet Noise Reduction in Computed Tomography", Medical Physics, Vol. 26, Issue 8, pp. 1600-1606, August 1999; Lee, et al., "Wavelet Methods for Inverting the Radon Transform with Noisy Data", IEEE Transactions on Image Processing, Vol. 10, Issue 1, pp. 79-94, January 2001; E. D. Kolaczyk, "Wavelet Shrinkage in Tomography", Engineering in Medicine and Biology Society, Proceedings of the 16th Annual International Conference of the IEEE, Vol. 2, pp. 1206-1207, 1994; and U.S. Pat. No. 5,461,655.

Similarly, one may apply wavelet transforms to projections (detector images), and isolate signals or features of interest (such as edges), causing the resulting reconstruction to correspond only to those features, see e.g., Srinivasa, et al., "Detection of Edges from Projections", IEEE Transactions on Medical Imaging, Vol. 11, Issue 1, pp. 76-80, March 1992; Warrick, et al., "Detection of Linear Features Using a Localized Radon Transform with a Wavelet Filter", Acoustics, Speech, and Signal Processing, 1997, ICASSP-97, 1997 IEEE International Conference, Vol. 4, pp. 2769-2772, 21-24 Apr. 1997; and U.S. Pat. No. 6,078,680.

As illustrated, wavelets have been investigated in a variety of algorithms related to tomographic image reconstruction. None of these algorithms provide a means, however, for accelerating a reconstruction method based on tomosynthesis, nor do they provide any means for accelerating an auto-focus algorithm. However, certain embodiments of the present invention provide a wavelet-based algorithm for tomosynthetic reconstruction of images and auto-focusing, which substantially reduces operational cost associated with the auto-focusing process.

Figure 6:
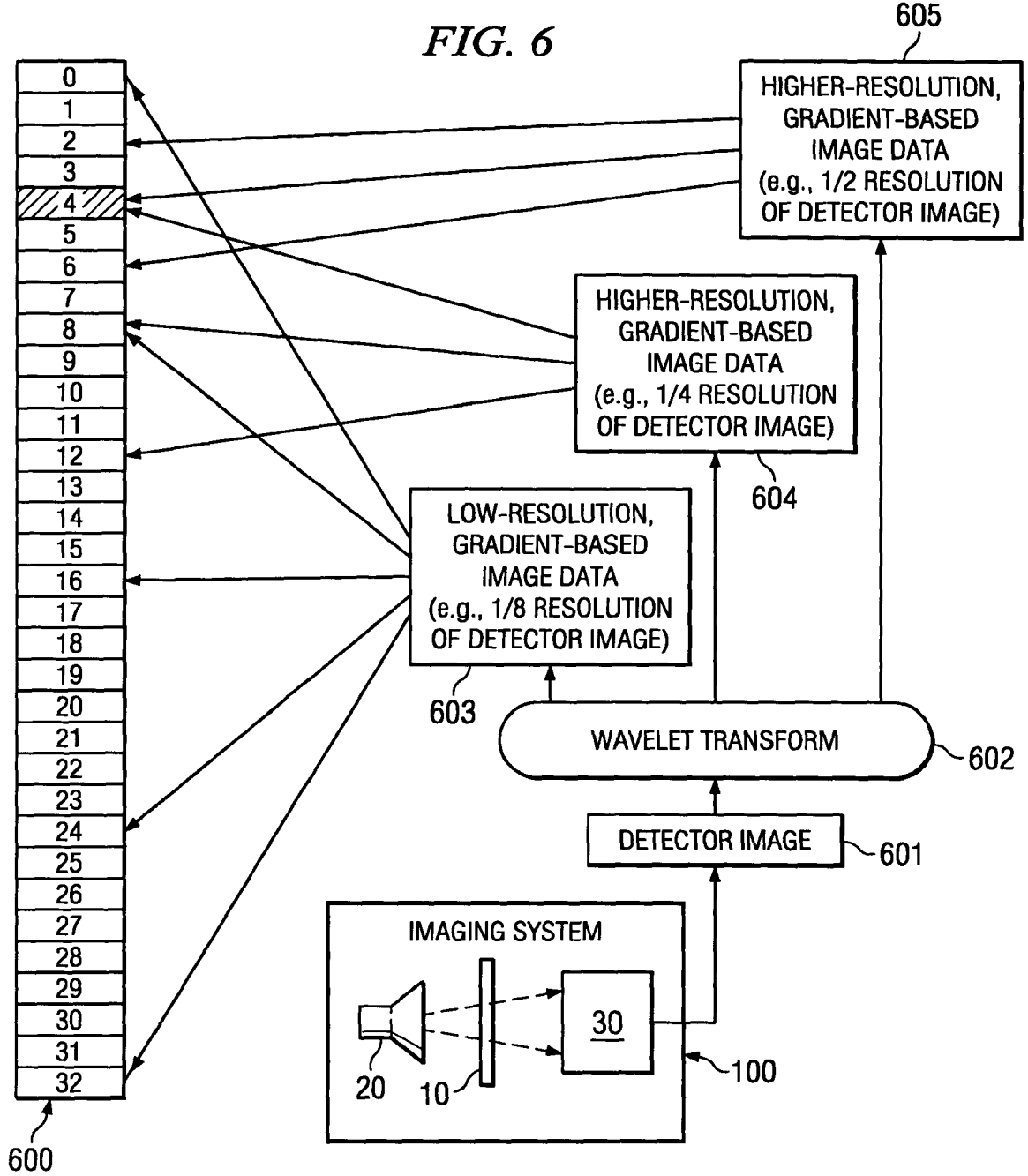
FIG. 6 shows an example block diagram illustrating one embodiment of the present invention.

An example auto-focusing technique according to an embodiment of the present invention is described hereafter in conjunction FIGS. 6-12. An example block diagram illustrating one embodiment of the present invention is shown in FIG. 6. According to this embodiment, detector image data is captured for an object under inspection, and such captured detector image data is used for computing gradient information for at least one depth layer of the object under inspection without first tomosynthetically reconstructing a full image of the depth layer(s). More specifically, a wavelet transform is computed for the captured detector image, and such wavelet transform is used to perform auto-focusing. More specifically, the wavelet transform is used to directly compute the gradient for at least one layer of an object under inspection, rather than first tomosynthetically reconstructing a full image of the depth layer and using the reconstructed image to compute the gradient. Such gradient that is computed directly from the wavelet transform may be used to identify a layer that includes an in-focus view of a feature of interest. Thus, this embodiment is computationally efficient in that the gradient of one or more depth layers in which a feature of interest may potentially reside may be computed and used for performing auto-focusing to determine the depth layer that includes an in-focus view of the feature of interest without requiring that the depth layers first be tomosynthetically reconstructed.

As described further hereafter, in certain embodiments (such as the example embodiment described with FIG. 6), the wavelet transform comprises gradient-based image data at a plurality of different resolutions. A hierarchical auto-focusing technique may be used in which the gradient-based image data having a first (e.g., relatively coarse) resolution may be used to evaluate at least certain ones of a plurality of depth layers in which a feature of interest may potentially reside to determine a region of layers in which an in-focus view of the feature of interest resides. Thereafter, the gradient-based image data having a finer resolution may be used to evaluate at least certain ones of the depth layers within the determined region to further focus in on a layer in which an in-focus view of the feature of interest resides.

Figure 7:
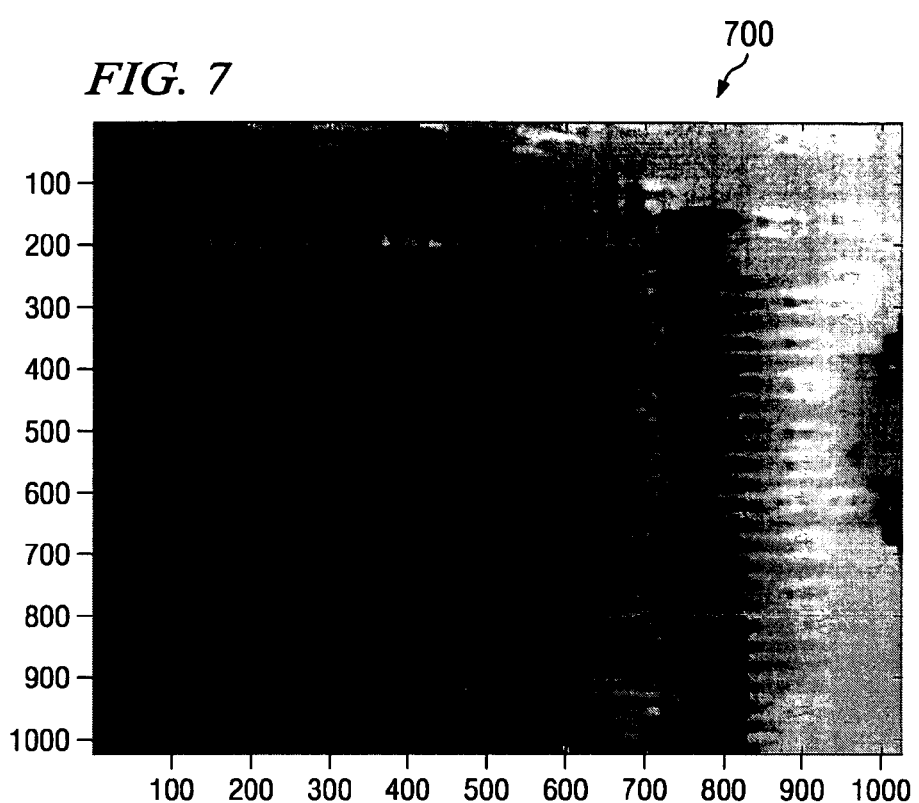
FIG. 7 shows a specific example of a typical detector image obtained from an X-ray imaging system, such as the example imaging systems of FIGS. 1A-1B and 2C.

For example, an imaging system 100, such as the example imaging systems described above in FIGS. 1A-1B and 2C, is used to capture detector image 601. For instance, source 20 of imaging system 100 projects X-rays toward an object 10 that is under inspection, and detector array 30 captures a detector image 601. A specific example of such a detector image captured for a portion of an integrated circuit is shown in FIG. 7, which is described further below.

In the example embodiment shown in FIG. 6, the detector image 601 is processed by a wavelet transform 602, such as the well-known 2D Haar wavelet transform. Wavelet transform 602 transforms detector image 601 into a representation of the image data at multiple different resolutions. More specifically, wavelet transform 602 transforms detector image 601 into gradient-based image data at a plurality of different resolutions, such as low-resolution gradient-based image data 603, higher-resolution gradient-based image data 604, and even high-resolution gradient-based image data 605. In this example, low-resolution gradient-based image data 603 is one-eighth (⅛) the resolution of detector image 601; higher-resolution gradient-based image data 604 is one-fourth (¼) the resolution of detector image 601; and even higher-resolution gradient-based image data 605 is one-half (½) the resolution of detector image 601.

In this manner, the result of processing detector image 601 with wavelet transform 602 provides gradient-based information in a hierarchy of resolutions. An embodiment of the present invention may use this hierarchy of resolutions of gradient-based image data to perform the auto-focusing operation. For instance, in the example of FIG. 6, any of 33 different depth layers 600 (numbered 0-32 in FIG. 6) of the object 10 under inspection may include an in-focus view of a feature that is of interest. That is, the specific location of the depth layer that includes the feature of interest is unknown. Suppose, for example, that the top surface of object 10 is of interest (e.g., for an inspection application). From the setup of the imaging system, the inspector may know approximately where that surface is (in the "Z" height dimension). In other words, the top surface of object 10 is expected to be found within some range $\Delta Z$. That range $\Delta Z$ is subdivided into several layers (e.g., the 32 layers 600 in FIG. 6), and the auto-focus algorithm is run on those layers 600 to identify the sharpest layer (the layer providing the sharpest image of the top surface of object 10 in this example). The number of layers may be empirically defined for a given application, and is thus not limited to the example number of layers 600 shown in FIG. 6.

As shown in the example of FIG. 6, the low-resolution gradient-based image data 603 is used to reconstruct the gradient of every eighth one of layers 600. Thus, tomosynthesis is performed using the gradient-based image data 603 to reconstruct the gradient of layers 0, 8, 16, 24, and 32. Those reconstructed layers are evaluated (e.g., for sharpness and/or other characteristics) to determine the layer that provides a most in-focus view of a feature of interest. For instance, the sharpness of those layers may be measured (by analyzing their reconstructed gradients), and the layer having the maximum sharpness may be determined. In the example of FIG. 6, layer 8 is determined as having the maximum sharpness.

It should be recognized that the gradients of layers 0, 8, 16, 24, and 32 are reconstructed directly from the relatively low-resolution image data 603 of the wavelet transform 602. Thus, the computational cost of reconstructing the gradient of such layers 0, 8, 16, 24, and 32 directly from this low-resolution data 603 is much less than first tomosynthetically reconstructing a cross-sectional image from the captured detector image 601 and then computing the gradient from such reconstructed cross-sectional image. The process of identifying the one layer out of every eighth layer of layers 600 that is closest to (or is most nearly) the layer of interest (e.g., the sharpest layer) may be referred to as the first level of the hierarchical auto-focusing technique.

Once the layer of the first level of the hierarchical auto-focusing technique that has the maximum sharpness is determined (layer 8 in the example of FIG. 6), the wavelet transform data having the next highest resolution may be used to further focus in on the layer of interest. For instance, as shown in the example of FIG. 6, the higher-resolution gradient-based image data 604 is used to reconstruct the gradients of certain layers around the initially identified layer 8 to further focus in on the layer of interest. In this example, the gradient-based image data 604 is used for reconstructing the gradient of layer 8, which was identified in the first level of the hierarchical auto-focusing technique as being nearest the layer of interest, and the gradient-based image data 604 is also used for reconstructing the gradients of layers 4 and 12. That is, tomosynthesis is performed using the gradient-based image data 604 (which is the next highest resolution gradient-based data in the hierarchy of resolution data of the wavelet transform) to reconstruct the gradients of layers 4, 8, and 12. The reconstructed gradients of layers 4, 8, and 12 are evaluated (e.g., for sharpness and/or other characteristics) to determine the layer that provides the most in-focus view of a feature of object 10 that is of interest. In the example of FIG. 6, layer 4 is determined as having the maximum sharpness.

It should be recognized that the gradients of layers 4, 8, and 12 are reconstructed directly from the gradient-based image data 604 of the wavelet transform 602. Thus, the computational cost of reconstructing the gradient of such layers 4, 8, and 12 directly from this data 604 is much less than first tomosynthetically reconstructing a cross-sectional image from the captured detector image 601 and then computing the gradient from such reconstructed cross-sectional image. The process of identifying the one layer out of layers 4, 8, and 12 of layers 600 that is closest to (or is most nearly) the layer of interest (e.g., the sharpest layer) may be referred to as the second level of the hierarchical auto-focusing technique.

Once the layer of the second level of the hierarchical auto-focusing technique having the maximum sharpness is determined from analysis of the reconstructed gradients using gradient-based image data 604 (layer 4 in the example of FIG. 6), the wavelet transform data having the next highest resolution may be used to further focus in on the layer of interest. For instance, as shown in the example of FIG. 6, the higher-resolution gradient-based image data 605 is used to reconstruct the gradient of certain layers around the identified layer 4 to further focus in on the layer of interest. In this example, the gradient-based image data 605 is used for reconstructing the gradient of layer 4, which was identified in the second level of the hierarchical auto-focusing technique as being nearest the layer of interest, and the gradient-based image data 605 is also used for reconstructing the gradient of layers 2 and 6. That is, tomosynthesis is performed using the gradient-based image data 605 (which is the next highest resolution gradient-based data in the hierarchy of resolution data of the wavelet transform) to reconstruct the gradients of layers 2, 4, and 6. Those layers are evaluated by the auto-focusing application (e.g., for sharpness and/or other characteristics) to determine the layer that provides the most in-focus view of a feature of object 10 that is of interest. For instance, the sharpness of those layers may again be measured by the auto-focusing application (using their reconstructed gradients), and the layer having the maximum sharpness may be determined. In the example of FIG. 6, it is determined that layer 4 is the layer of interest (i.e., is the layer having the maximum sharpness).

It should be recognized that in the above example auto-focusing process of FIG. 6, the gradient of layers 2, 4, and 6 are reconstructed from the gradient-based image data 605 of the wavelet transform 602. Thus, the computational cost of reconstructing the gradient of such layers 2, 4, and 6 directly from this data 605 is much less than first tomosynthetically reconstructing a cross-sectional image from the captured detector image 601 and then computing the gradient from such reconstructed cross-sectional image. The process of identifying the one layer out of layers 2, 4, and 6 of layers 600 that is closest to (or is most nearly) the layer of interest (e.g., the sharpest layer) may be referred to as the third level of the hierarchical auto-focusing technique.

Any number of depth layers 600 may be evaluated by the auto-focusing application in alternative implementations, and any number of levels of processing may be included in the hierarchy in alternative implementations (and thus are not limited solely to the example of three levels of hierarchical processing described with FIG. 6). Also, while an example hierarchical auto-focusing process is described with FIG. 6, it should be recognized that other embodiments of the present invention may not utilize such a hierarchical technique. For instance, certain alternative embodiments of the present invention may use gradient-based image data from wavelet transform 602 (e.g., higher-resolution gradient-based image data 605) to reconstruct (or compute) the gradient for every one of layers 600, and such gradients may be evaluated to determine the layer of interest (e.g., the layer that provides the most in-focus view of a feature of object 10 that is of interest). Because the gradients of such layers are reconstructed directly from wavelet transform 602 without requiring that those layers first be tomosynthetically reconstructed, these alternative embodiments may also be more computationally efficient than traditional auto-focusing technqiues.

FIG. 7 shows a specific example of a typical projection (detector) image as might be obtained from an X-ray imaging system, such as the 5DX system available from Agilent Technologies or the example imaging systems described above in FIGS. 1A-1B and 2C. More specifically, in this example, image 700 is a raw image of a portion of an integrated circuit (or "chip") that is coupled to a circuit board, such as may be captured by detector array 30 of the example imaging system of FIGS. 1A-1B.

Image 700 is shown at relatively high resolution, approximately 1000 pixels by 1000 pixels in this example, so that the small features that are of interest can be clearly seen and/or analyzed. Thus, in many applications, such as industrial inspection applications, an image may be captured by an imaging system at a relatively high resolution (e.g., 1000 pixels by 1000 pixels) to enable sufficiently high-resolution images to be reconstructed for analysis of the object. However, the resolution needed for analyzing the object under inspection (e.g., the resolution needed for a given application, such as inspection of the object) is often greater than the resolution needed for performing auto-focusing in accordance with an embodiment of the present invention. Thus, images at such a high resolution (e.g., 1000 pixels by 1000 pixels) as may be needed for an application, such as inspection, is not needed for the auto-focusing algorithm of an embodiment of the present invention. Accordingly, as described further below, lower-resolution images may be used to identify the layer(s) of interest (e.g., layer(s) that include a feature of interest and are in focus), and then those layer(s) of interest may be reconstructed into images of higher resolution. The layers that are determined to not be of interest (e.g., are not in focus) are not required to be reconstructed at such higher resolution. Thus, a layer that includes a feature of interest and is in focus may be identified by the auto-focusing algorithm. As described further below, such an auto-focusing algorithm reduces the computational burden associated with the auto-focusing process.

According to an embodiment of the present invention, a wavelet transform is used to transform the detected image data to a representation of the image data at multiple different resolutions. As described further below, in certain embodiments, a wavelet transform is used to transform the detected image data to a plurality of different resolutions that each include gradient information, and such gradient information may be used in performing auto-focusing to identify the layer(s) of interest (e.g., the layer(s) that provide an in-focus view of feature(s) that are of interest). An example application of such a wavelet transform according to one embodiment of the present invention is described further below with FIG. 8.

Figure 8:
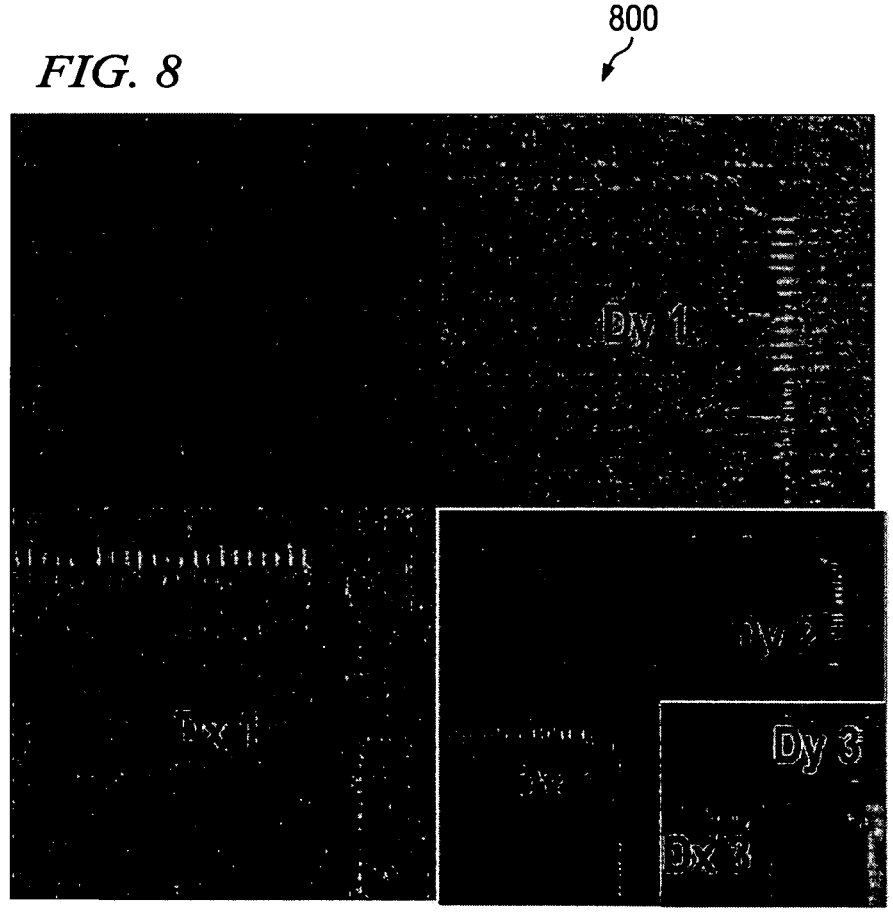
FIG. 8 shows the result of processing the example detector image of FIG. 7 with a 2D Haar wavelet transform.

FIG. 8 shows the example image 700 of FIG. 7 after application of a 2D Haar wavelet transform, which is a well-known wavelet transform in the art of image processing. More particularly, FIG. 8 shows the result of processing the raw, detected image data 700 with a 2D Haar wavelet transform. It should be recognized that the off-diagonal blocks of the wavelet representation 800 of FIG. 8 contain horizontal and vertical gradients of the detector image 700. As described further below, these raw gradient images may be used in tomosynthesis reconstruction to directly produce a gradient image of the final, reconstructed image.

In particular, block Dx1 of FIG. 8 contains a representation of the horizontal gradient of the original detector image 700, obtained using a filter similar to the Sobel filter. Block Dy1 represents the vertical gradient. Blocks Dx2 and Dy2 contain representations of the gradient at a coarser resolution. At subsequent levels, the Dx and Dy blocks contain gradient information at still coarser resolutions, as in the blocks Dx3 and Dy3 shown in FIG. 8. In general, the gradient information in those blocks having coarser resolution, such as Dx3 and Dy3 more accurately represent the gradient of larger features, since the filtering is effectively computed over a larger area of the image.

Thus, the Dx1 and Dy1 blocks of the resulting wavelet transform 800 in the example of FIG. 8 correspond to the gradient of the detector image 700 (of FIG. 7) at half the resolution of such detector image 700. That is, the Dx1 and Dy1 blocks of the resulting wavelet transform of the detector image 700 may be used to compute the Dx1 and Dy1 blocks of a tomosynthetically reconstructed image. Blocks Dx2 and Dy2 of the resulting wavelet transform correspond to the gradient of the detector image 700 (of FIG. 7) at still a coarser resolution than that of blocks Dx1 and Dy1 (e.g., at one-fourth the resolution of the detector image 700 of FIG. 7). Further blocks, such as blocks Dx3 and Dy3 (which are at one-eighth the resolution of the detector image 700 of FIG. 7 in this example), that correspond to the gradient at progressively coarser resolution may also be included in the resulting wavelet transform 800.

As described above, traditional auto-focus algorithms first tomosynthetically reconstruct a layer of an object under inspection, and then compute the gradient of that reconstructed layer. The computed gradient of the reconstructed layer is then used in performing the auto-focus operation (see operational steps 2-4 in the traditional auto-focus algorithm described above). As is well-known in the art, the gradient essentially is the derivative of the image. So, the auto-focus algorithm is essentially attempting to locate edges within the image. By computing the derivative of the image, the locations with sharp edges are enhanced.

It should be recognized that the resulting wavelet transform 800 of FIG. 8 includes blocks Dx1 and Dy1 that may be used to reconstruct the X and the Y derivative of the detector image 700 (of FIG. 7). Such Dx1 and Dy1 have less resolution than that of the detector image 700 of FIG. 7 (e.g., Dx1 and Dy1 have half the resolution of such detector image 700). Also, blocks Dx2 and Dy2 in the wavelet transform may be used to reconstruct the X and Y derivative of the detector image 700 at even coarser resolution (e.g., one-fourth the resolution of detector image 700), and blocks Dx3 and Dy3 in the wavelet transform may be used to reconstruct the X and Y derivative of the detector image 700 at even coarser resolution (e.g., one-eighth the resolution of detector image 700). Again, the full, reconstructed image (resulting from the tomosynthetic reconstruction process) need not be first reconstructed before obtaining the X and Y derivatives, but rather those X and Y derivatives are available in the resulting wavelet transform that is produced through processing of the raw detected image data 700. Thus, in an embodiment of the present invention, an auto-focus algorithm may be implemented to use the gradient information available in the resulting wavelet transform to perform auto-focusing. Accordingly, a full image of the layers of an object need not be reconstructed before performing auto-focusing to identify the layer(s) that are of interest (e.g., that includes an in-focus view of a feature of interest). Further, lower-resolution image data than that of the tomosynthetically reconstructed image or the detector image 700 (e.g., the coarse resolution of blocks Dx1 and Dy1, Dx2 and Dy2, and/or Dx3 and Dy3) may be used in performing the auto-focusing operation.

Accordingly, by using the result of a wavelet transform for performing the auto-focusing operation, rather than first fully reconstructing an image of each layer in which a feature of interest may potentially reside and processing such reconstructed images for performing auto-focusing, lower-resolution images may be used for performing the auto-focusing. Auto-focusing can typically be performed at a lower resolution than that desired for the captured detector image 700 and/or the fully reconstructed images of the layer(s) of interest. Thus, the computational cost associated with the auto-focusing process of embodiments of the present invention is reduced below that of traditional auto-focusing techniques. Further, the wavelet transform 800 provides gradient-based image data, which is useful for the auto-focus processing because, as described above, the auto-focus algorithm can use such gradient-based image data to identify the layer(s) of interest (i.e., the layer(s) that are in focus).

Thus, the example wavelet transform of FIG. 8 provides gradient-based image data 800 at a plurality of different resolutions. More specifically, in the example of FIG. 8, Dx3 and Dy3 provide gradient-based image data at the coarsest scale (e.g., one-eighth the resolution of the detector image 700 of FIG. 7). Dx2 and Dy2 provide gradient-based image data at a higher resolution than that of Dx3 and Dy3 (e.g., the resolution of Dx2 and Dy2 in this example is one-fourth the resolution of the detector image 700 of FIG. 7), and Dx1 and Dy1 provide gradient-based image data at a higher resolution than that of Dx2 and Dy2 (e.g., the resolution of Dx1 and Dy1 in this example is one-half the resolution of the detector image 700 of FIG. 7). In this manner, the wavelet transform 800 includes gradient-based information in a hierarchy of resolutions. An embodiment of the present invention may use this hierarchy of resolutions of gradient-based image data to perform the auto-focusing operation, such as described further below with the example of FIG. 9.

Figure 9:
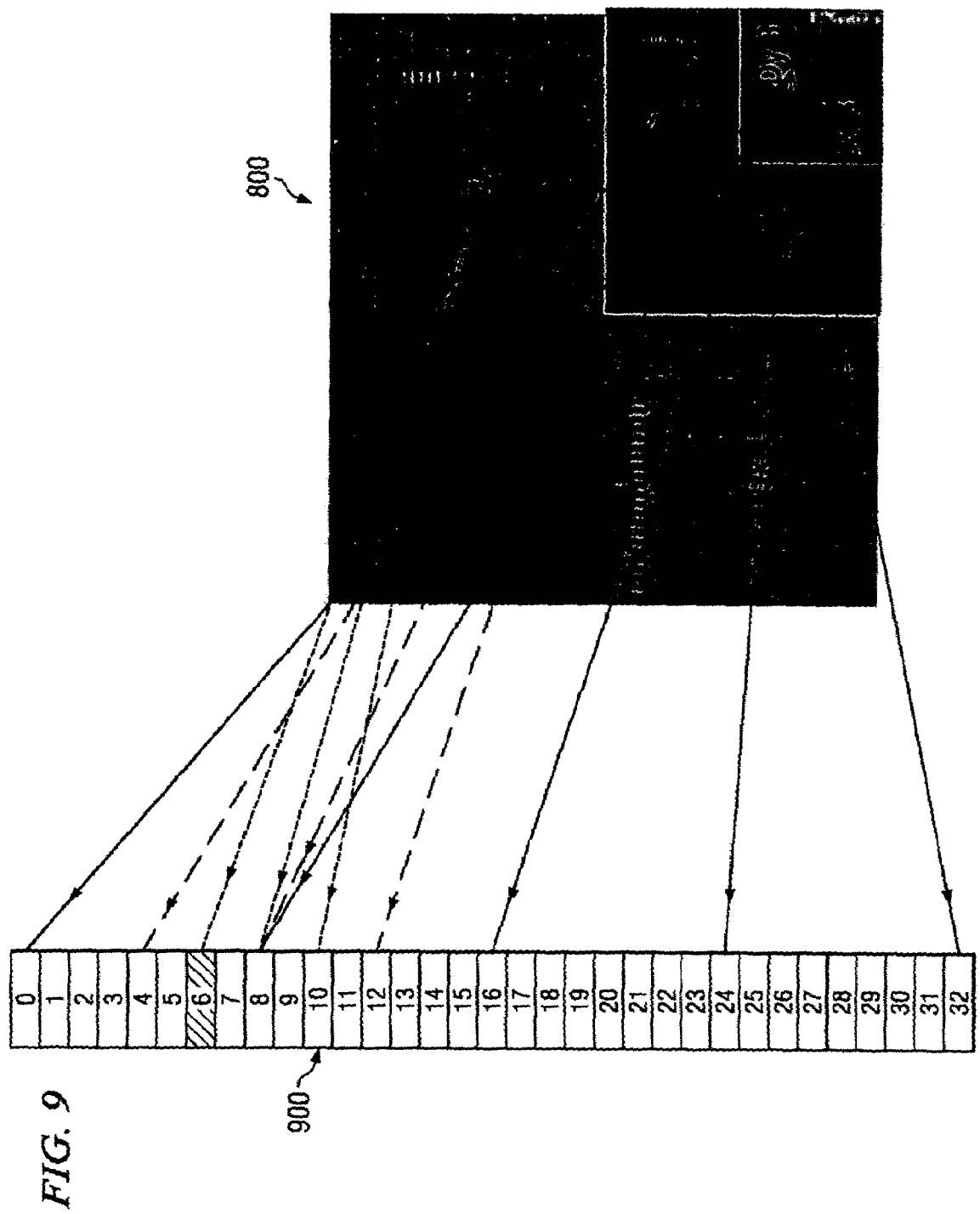
FIG. 9 shows an example hierarchical organization of one embodiment of an auto-focus algorithm, which uses the resulting wavelet transform of FIG. 8.

FIG. 9 shows a hierarchical organization of one embodiment of the auto-focus algorithm. Tomosynthesis is applied to the Dx and Dy blocks of wavelet transform 800 to reconstruct the gradient at a plurality of different resolutions. As described further below, in this embodiment of the auto-focus algorithm not every layer may be reconstructed using every resolution block. In particular, fine resolution blocks can reconstruct more layers than can coarse resolution blocks. This is due to the fact that the resolution of projection images in the X and Y directions (i.e., horizontal, vertical directions) is directly related to the resolution of layers in the Z direction (i.e., height discrimination). This aspect may be used to an advantage in this embodiment of the algorithm, as described further below.

According to one embodiment, the lowest resolution gradient-based image data included in the wavelet transform 800 (e.g., Dx3 and Dy3 in the example of FIG. 8) is used to reconstruct the gradient of certain layers of an object in an attempt to identify a region of layers in which a desired layer (e.g., a layer that includes an in-focus view of a feature of interest) likely resides. For instance, in the example of FIG. 9, any of 33 different layers 900 (numbered 0-32 in FIG. 9) of the object under inspection may be reconstructed from the captured image data 700.

It should be appreciated that the 32 layers 900 in the example of FIG. 9 arise from the uncertainty in the location of the layer of interest. Suppose, for example, that the top surface of a circuit board under inspection is of interest (e.g., for an inspection application). From the setup of the imaging system, the inspector may know approximately where that surface is (in the "Z" height dimension). In other words, the top surface of the board is expected to be found within some range $\Delta Z$. That range $\Delta Z$ (in which the top surface of the board may potentially reside) is subdivided into several layers (e.g., the 32 layers 900 in FIG. 9), and the auto-focus algorithm is run on those layers 900 to identify the sharpest layer (the layer providing the sharpest image of the top surface of the board in this example). The number of layers may be empirically defined for a given application, and is thus not limited to the example number of layers 900 shown in FIG. 9. For instance, if the uncertainty in position of the feature of interest (e.g., the top surface of the circuit board in this example) is large (a large $\Delta Z$), then the number of layers 900 may be large (e.g., more than the number shown in FIG. 9), and the auto-focusing techniques described herein may be used to determine a layer of focus within such layers. Further, embodiments of the present invention may be utilized in applications in which there is virtually no information about the location of the feature(s) of interest. For instance, the entire range of possible Z locations within an imaging system at which a feature of interest may reside (a very large $\Delta Z$) may be subdivided into thousands of layers, and the example auto-focusing techniques described herein may be used to find a layer that provides an in-focus view of the feature of interest (e.g., the top surface of a circuit board under inspection).

As shown in the example of FIG. 9, the Dx3 and Dy3 blocks of the wavelet transform 800 are used to reconstruct the gradient of every eighth layer of the object. While the arrows are shown in FIG. 9 for using Dy3 for reconstructing the gradient (i.e., the Y gradient) of every eighth layer of the object under inspection, it should be recognized that Dx3 is also used for reconstructing the gradient (i.e., the X gradient) of those layers of the object. Thus, tomosynthesis is performed using the Dx3 and Dy3 image data (which is low-resolution gradient-based data) to reconstruct the gradient of layers 0, 8, 16, 24, and 32. Those reconstructed layers are evaluated (e.g., for sharpness and/or other characteristics) to determine the layer that is "closest" to (or is most nearly) the desired layer (e.g., is the layer that provides a most in-focus view of a feature of interest). For instance, the sharpness of those layers may be measured (by analyzing their reconstructed gradients), and the layer having the maximum sharpness may be determined. In the example of FIG. 9, layer 8 is determined as having the maximum sharpness.

It should be recognized that the gradients of layers 0, 8, 16, 24, and 32 are reconstructed from the relatively low-resolution image data of the Dx3 and Dy3 blocks of the wavelet transform 800. Thus, the computational cost of reconstructing the gradient of such layers 0, 8, 16, 24, and 32 using this low-resolution data of Dx3 and Dy3 is much less than reconstructing a full, high-resolution image of those layers. Also, the computational cost of reconstructing the gradient of layers 0, 8, 16, 24, and 32 using the low-resolution data of Dx3 and Dy3 is less than reconstructing the gradient of those layers using the higher-resolution image data of either Dx2 and Dy2 or Dx1 and Dy1. Further, at any resolution, the computational cost of reconstructing the gradient images directly from the captured detector image 700 is less than for first tomosynthetically reconstructing a cross-sectional image from the captured detector image and then computing the gradient from such reconstructed cross-sectional image. The process of identifying the one of those layers reconstructed using the Dx3 and Dy3 image data that is closest to (or is most nearly) the layer of interest (e.g., the sharpest layer) may be referred to as the first level of the hierarchical auto-focusing technique.

Once the layer of the first level of the hierarchical auto-focusing technique that has the maximum sharpness is determined (layer 8 in the example of FIG. 9), the wavelet transform data having the next highest resolution may be used to further focus in on the layer of interest. For instance, as shown in the example of FIG. 9, the Dx2 and Dy2 image data is used to reconstruct the gradients of certain layers around the initially identified layer 8 to further focus in on the layer of interest. In this example, the Dx2 and Dy2 image data is used for reconstructing the gradient of layer 8, which was identified in the first level of the hierarchical auto-focusing technique as being nearest the layer of interest, and the Dx2 and Dy2 image data is also used for reconstructing the gradients of layers 4 and 12. That is, tomosynthesis is performed using the Dx2 and Dy2 image data (which is the next highest resolution gradient-based data in the hierarchy of resolution data of the wavelet transform) to reconstruct the gradients of layers 4, 8, and 12. The reconstructed gradients of layers 4, 8, and 12 are evaluated (e.g., for sharpness and/or other characteristics) to determine the layer that is "closest" to (or is most nearly) the desired layer (e.g., shows the most in-focus view of a feature of interest). For instance, the sharpness of those layers may again be measured, and the layer having the maximum sharpness may be determined from evaluation of the reconstructed gradients. In the example of FIG. 9, layer 8 is again determined as having the maximum sharpness.

It should be recognized that the gradients of layers 4, 8, and 12 are reconstructed from the relatively low-resolution image data of the Dx2 and Dy2 blocks of the wavelet transform 800. Thus, the computational cost of reconstructing the gradients of such layers 4, 8, and 12 using this low-resolution data of Dx2 and Dy2 is much less than reconstructing a full, high-resolution image of those layers. Also, the computational cost of reconstructing the gradients of layers 4, 8, and 12 using the low-resolution data of Dx2 and Dy2 is less than reconstructing the gradients of those layers using the higher-resolution image data of Dx1 and Dy1. Further, at any resolution, the computational cost of reconstructing the gradient images directly from the captured detector image 700 is less than for first tomosynthetically reconstructing a cross-sectional image from the captured detector image and then computing the gradient from such reconstructed cross-sectional image. The process of identifying the one of those layers reconstructed using the Dx2 and Dy2 image data that is closest to (or is most nearly) the layer of interest (e.g., the sharpest layer) may be referred to as the second level of the hierarchical auto-focusing technique.

Once the layer of the second level of the hierarchical auto-focusing technique having the maximum sharpness is determined from analysis of the reconstructed gradients using Dx2 and Dy2 (layer 8 in the example of FIG. 9), the wavelet transform data having the next highest resolution may be used to further focus in on the layer of interest. For instance, as shown in the example of FIG. 9, the Dx1 and Dy1 image data is used to reconstruct the gradient of certain layers around the identified layer 8 to further focus in on the layer of interest. In this example, the Dx1 and Dy1 image data is used for reconstructing the gradient of layer 8, which was identified in the second level of the hierarchical auto-focusing technique as being nearest the layer of interest, and the Dx1 and Dy1 image data is also used for reconstructing the gradient of layers 6 and 10. That is, tomosynthesis is performed using the Dx1 and Dy1 image data (which is the next highest resolution gradient-based data in the hierarchy of resolution data of the wavelet transform) to reconstruct the gradients of layers 6, 8, and 10. Those layers are evaluated (e.g., for sharpness and/or other characteristics) to determine the layer that is "closest" to (or is most nearly) the desired layer. For instance, the sharpness of those layers may again be measured (using their reconstructed gradients), and the layer having the maximum sharpness may be determined. In the example of FIG. 9, it is determined that layer 6 is the layer of interest (i.e., is the layer having the maximum sharpness).

It should be recognized that in the above example auto-focusing process of FIG. 9, the gradient of layers 6, 8, and 10 are reconstructed from the relatively low-resolution image data of the Dx1 and Dy1 blocks of the wavelet transform 800. Thus, the computational cost of reconstructing the gradient of such layers 6, 8, and 10 using this low-resolution data of Dx1 and Dy1 is much less than reconstructing a full, high-resolution image of those layers. The process of using the Dx1 and Dy1 image data of wavelet transform 800 to identify the one of layers 6, 8, and 10 that is closest to (or is most nearly) the layer of interest (e.g., the sharpest layer) may be referred to as the third level of the hierarchical auto-focusing technique.

In certain embodiments, an optional fourth level of the hierarchical auto-focusing technique may be used, wherein the captured detector image 700 is used to reconstruct layers 5, 6, and 7 to determine the layer that is most in focus. That is, the above process described with FIG. 9 may be used to identify layer 6 as a layer having the maximum sharpness, but layers 5 and 7 have not yet been evaluated. Thus, layer 6 and the layer on either side thereof (layers 5 and 7) may be reconstructed from the captured detector image 700, and the reconstructed images may be analyzed to detect which of those layers provides the sharpest view of a feature of interest. Thus, even when using this optional fourth level of processing, every potential layer 900 in which a feature of interest may reside are not required to be reconstructed. Further, gradients for various layers are reconstructed directly from the captured detector image and used for zoning in on the layer that is most in focus. Once a layer that is most in focus is identified using the wavelet transform 800 of a captured detector image 700 (such as layer 6 in the example of FIG. 9), that layer as well as the layer on either side thereof may be reconstructed using the detector image 700 to further refine the height of the correct layer. For many applications, this further refinement may be unnecessary, and thus the layer identified through analysis of the gradients reconstructed from the wavelet transform 800 of detector image 700 as being the sharpest image (e.g., layer 6 in the example of FIG. 9) may be returned as the layer of focus by the auto-focus algorithm.

Figure 10:
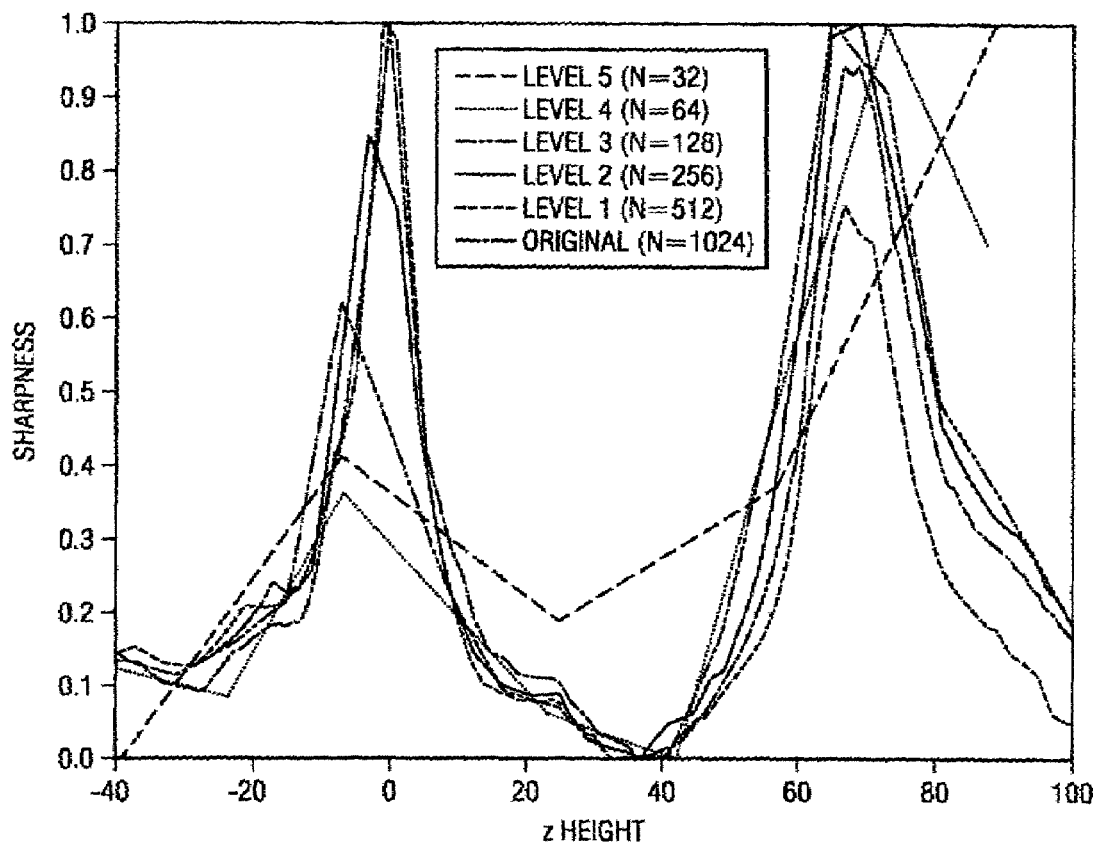
FIG. 10 shows the result of sharpness calculations using various blocks of the wavelet transform of FIG. 8 according to one embodiment of an auto-focus algorithm.

FIG. 10 shows the result of sharpness calculations using various blocks of the wavelet transform 800 of FIG. 8 according to one embodiment of the auto-focus algorithm. It is demonstrated that even coarse resolution blocks may be used to effectively determine the sharpness profile of layers. In fact, as mentioned above, the coarse-scale blocks may give superior results since the gradient is effectively computed over larger areas, which may be more appropriate for larger features. Also, since the coarse resolution blocks are smaller, the computational burden at those coarser resolutions is dramatically reduced. Further, at any resolution, the computational cost of reconstructing the gradient images directly from the captured detector image 700 is less than for first tomosynthetically reconstructing a cross-sectional image from the captured detector image 700 and then computing the gradient from such reconstructed cross-sectional image.

As described above, according to one embodiment of the present invention, an auto-focusing algorithm is provided wherein tomosynthesis is used to reconstruct sub-blocks of projection images, after application of a wavelet transform. In this approach, entire images do not need to be reconstructed at each layer. Only certain of the off-diagonal sub-blocks (e.g., those labeled as Dx or Dy in FIG. 8) need to be used in the reconstruction process. The total cost of this embodiment of the auto-focus algorithm will depend on how many sub-blocks are used. For example, a reconstruction using very coarse (small) blocks may be used to rapidly estimate the sharpness profile of the various layers, and finer scale blocks may be used to selectively refine the sharpness profile, such as in the example hierarchical process described above in conjunction with FIG. 9. While three hierarchical layers are described in the example of FIG. 9 corresponding to use of three progressively higher-resolution portions of wavelet transform 800, in other implementations any number of progressively higher-resolution blocks may be included in wavelet transform 800 and any number of such blocks may be used in the auto-focusing process (e.g., the hierarchical process may include more than three levels).

Figure 11:
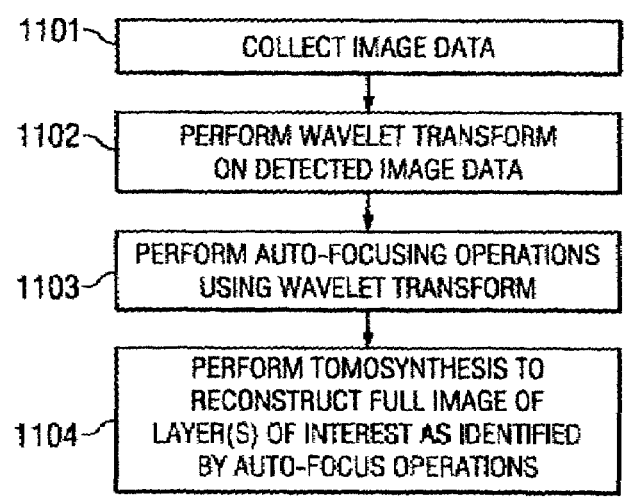
FIG. 11 shows an example operational flow diagram of one embodiment of the present invention.

Turning to FIG. 11, an example operational flow diagram of one embodiment of the present invention is shown. As shown, in operational block 1101, raw image data is detected by an imaging system, such as that of FIG. 2C, and is collected. More specifically, 2D image data (pixels), such as detector image 700 of FIG. 7, is captured by an imaging system in operational block 1101. In operational block 1102, a wavelet transform is performed on the detected image data. In operational block 1103, auto-focusing operations are performed using the wavelet transform data blocks. That is, auto-focusing operations are performed to identify one or more layers of interest (e.g., one or more layers that include a feature of interest in focus). As shown in dashed line (as being optional), operational block 1104 may then perform tomosynthesis to reconstruct a full, high-resolution image of the layer(s) of interest identified by the auto-focus operations.

Figure 12:
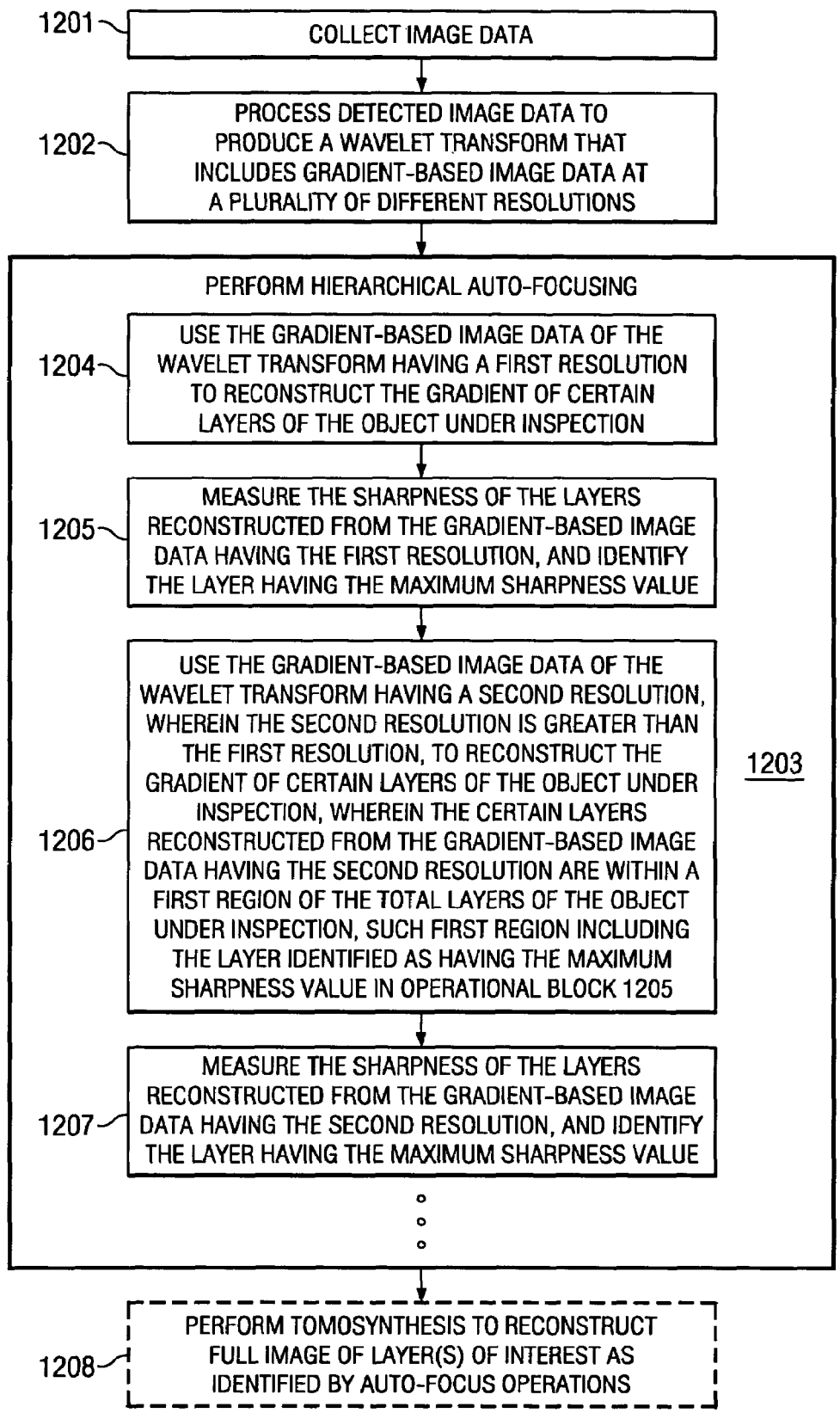
FIG. 12 shows another example operational flow diagram of an embodiment of the present invention.

FIG. 12 shows another example operational flow diagram of an embodiment of the present invention. As shown, in operational block 1201, raw image data, such as detector image 700 of FIG. 7, is detected by an imaging system, such as that of FIG. 2C, and is collected. More specifically, 2D image data is captured by an imaging system and is collected (e.g., by a processing unit for performing auto-focusing operations) in operational block 1201. In operational block 1202, the collected image data is processed to produce a wavelet transform that includes gradient-based image data at a plurality of different resolutions, such as Dx1 and Dy1, Dx2 and Dy2, and Dx3 and Dy3 of the example wavelet transform 800 of FIG. 8.

In operational block 1203, the gradient-based image data of the wavelet transform is used to perform hierarchical auto-focusing. More particularly, in this example embodiment, the gradient-based image data of the wavelet transform having a first resolution (e.g., Dx3 and Dy3 in the example of wavelet transform 800 of FIG. 8) is used to reconstruct the gradient of certain layers of the object under inspection (via tomosynthesis) in block 1204. In block 1205, the sharpness of each of the layers reconstructed from the gradient-based image data having the first resolution is measured, and the layer having the maximum sharpness value is identified.

In operational block 1206, the gradient-based image data of the wavelet transform having a second resolution that is greater than the first resolution (e.g., Dx2 and Dy2 in the example of wavelet transform 800 of FIG. 8) is used to reconstruct the gradient of certain layers of the object under inspection (via tomosynthesis). The certain layers reconstructed in block 1206 are within a first region of the total layers of the object under inspection, wherein the first region includes the layer identified as having the maximum sharpness in block 1205. For instance, in the example of FIG. 9 described above, Dx3 and Dy3 are used to reconstruct the gradient of certain layers 0, 8, 16, 24, and 32 (in accordance with the operation of block 1204 of FIG. 12), and it is determined that layer 8 has maximum sharpness (in accordance with the operation of block 1205 of FIG. 12). Then, Dx2 and Dy2 are used to reconstruct the gradient of certain layers that reside within a region (or "portion" or "sub-set") of layers 900, wherein such region includes layer 8. More specifically, in the example of FIG. 9 the gradients of layers 4, 8, and 12 are reconstructed using Dx2 and Dy2 (in accordance with the operation of block 1206 of FIG. 12). Layers 4, 8, and 12 reside within the upper half of layers 900 (i.e., within the region of layers 0-16).

In block 1207, the sharpness of each of the layers reconstructed from the gradient-based image data having the second resolution is measured, and the layer having the maximum sharpness value is identified. As described above with FIG. 9, various other levels of such hierarchical auto-focusing may be performed. Once the layer(s) of interest are identified by the hierarchical auto-focusing of block 1203, operation may advance to block 1208 (shown in dashed-line as being optional) to perform tomosynthesis to reconstruct a full, high-resolution image of the layer(s) of interest identified by the auto-focus operations.

Figure 13:
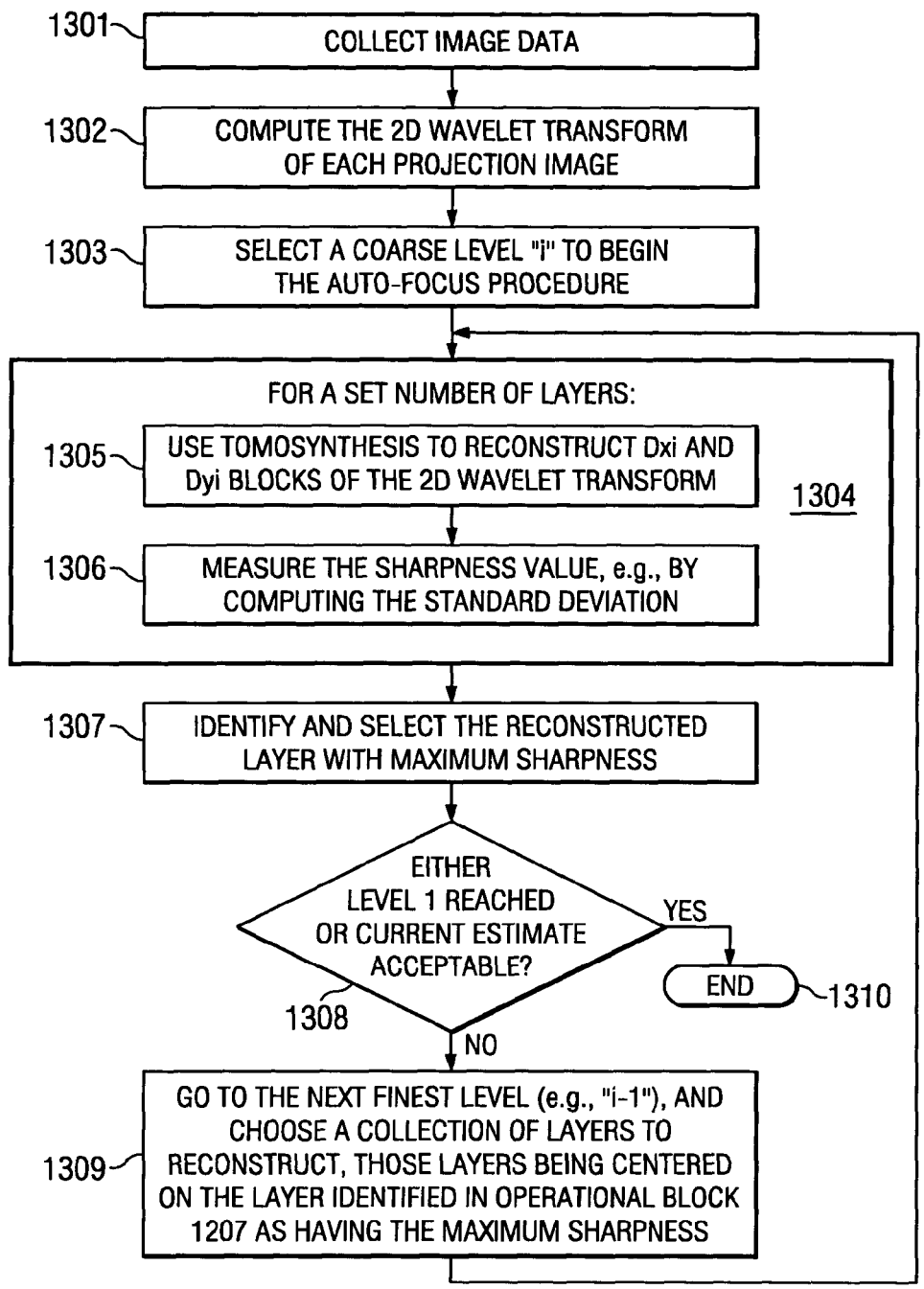
FIG. 13 shows yet another example operational flow diagram of an embodiment of the present invention.

Turning to FIG. 13, yet another example operational flow diagram of an embodiment of the present invention is shown. In operational block 1301, raw image data, such as detector image 700 of FIG. 7, is detected by an imaging system, such as that of FIG. 2C, and is collected by a processing system for performing auto-focusing operations. More specifically, radiographic image data at various different projections (or angles of view) is captured by an imaging system is collected in operational block 1301. In operational block 1302, the collected image data is processed to compute a 2D wavelet transform of each projection image. Such 2D wavelet transform includes gradient-based image data at a plurality of different resolutions (or "coarse levels"), such as Dx1 and Dy1, Dx2 and Dy2, and Dx3 and Dy3 of the example wavelet transform 800 of FIG. 8.

In operational block 1303, an initial coarse level "i" is selected for use in the initial level of the hierarchical auto-focus procedure. In operational block 1304, for a set number of layers, blocks 1305 and 1306 are performed. In operational block 1305, tomosynthesis is used to reconstruct the Dxi and Dyi blocks of the 2D wavelet transform. That is, the Dxi and Dyi blocks of the 2D wavelet transform are used in tomosynthesis to reconstruct the gradient of the set number of layers. In operational block 1306, the sharpness value of each reconstructed layer is measured, e.g., by computing the standard deviation.

In block 1307, the auto-focus algorithm identifies and selects the reconstructed layer with maximum sharpness. In operational block 1308, the auto-focus algorithm determines whether either level 1 is reached (i.e., whether reconstruction has been performed using the highest-resolution gradient-based image data available in the wavelet transform) or the current estimate of the layer of interest is acceptable for a user or a given application. If not, then operation advances to block 1309 whereat the next finest level (or next highest resolution) image data available in the wavelet transform is selected for use in reconstructing the gradient of a collection of layers that are centered on the layer identified in operational block 1307 as having the maximum sharpness. Operation then returns to block 1304 to reconstruct the collection of layers using the next finest level image data available in the wavelet transform and (in operational block 1307) identify the one of those collection of reconstructed layers that has the maximum sharpness. Once it is determined in block 1308 that either the finest level of resolution available in the wavelet transform has been utilized or the current estimated result from block 1307 is acceptable, the auto-focus process may end in block 1310.

Figure 14:
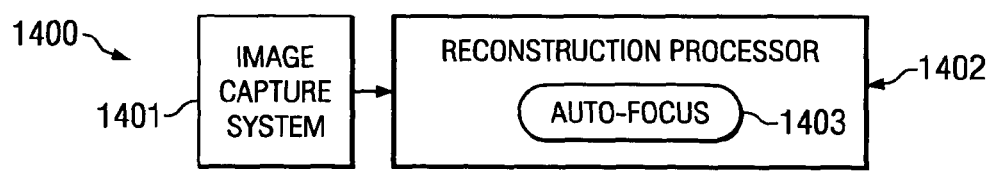
FIG. 14 shows an example block-diagram representation of a system on which embodiments of the present invention may be implemented.

FIG. 14 shows an example block-diagram representation of a system 1400 on which embodiments of the present invention may be implemented. As shown, an image capture system 1401 is included, which may comprise a radiographic image detection system such as that of FIGS. 1A-1B or 2C described above. The detector array of capture system 1401 outputs 2D image data (pixels) to reconstruction processor 1402. Reconstruction processor 1402 may be operable to perform tomosynthetic reconstruction of the 2D image data to generate reconstructed 3D image data (or layers). Reconstruction processor 1402 may be operable to execute an auto-focus process 1403 to perform auto-focusing in the manner described herein. Thus, system 1400 represents an example system which may perform the operations described in the example flows of FIGS. 11, 12, and 13. An auto-focus application (or process) 1403 for performing auto-focusing operations as described herein may be implemented in software, hardware, or a combination thereof. For instance, an auto-focus application may be implemented (e.g., in software executable by a processor, such as processor 1402) for computing a wavelet transform for received detector image data and for using such wavelet transform to compute gradient information for one or more depth layers of an object under inspection (such as depth layers 600 of FIG. 6). Thus, reconstruction processor 1402 may be implemented as an auto-focusing processor that is operable to perform auto-focusing operations, as well as tomosynthetic reconstruction operations. Alternatively, a separate auto-focusing processor may be implemented to perform auto-focusing operations. Of course, other system configurations than that represented by the example of FIG. 14 may be utilized that enable radiographic image data to be captured and processed by an auto-focusing algorithm of an embodiment of the present invention.

It should be recognized that various embodiments of the present invention provide advantages over traditional auto-focusing techniques. For example, in certain embodiments, a full, high-resolution image reconstruction does not need to be performed for each layer of an object under inspection in order to perform auto-focusing. Additionally, in certain embodiments, the gradient of images may be pre-computed (in a wavelet transform), so that a gradient filter does not need to be applied during auto-focusing. Also, in certain embodiments, the gradient is computed at several resolutions so that features of different sizes may be accurately represented.

Further, in accordance with certain embodiments of the present invention, the computational burden of the auto-focusing algorithm may be reduced significantly over that of traditional auto-focusing techniques. As an example, the computational cost for the example hierarchical auto-focus algorithm described above in conjunction with FIGS. 9 and 13 may generally be estimated as $(2.67P+18)MN+((2P+3)MN))(L_1/4+L_2/16+\ldots)$ where P is the number of projection images, M×N is the number of pixels in the reconstructed image, and Li is the number of layers computed at a particular resolution. A typical value for Li in one embodiment of the present invention is 3 to 5, although other values may be used as desired for certain applications. For the specific case in which 16 projection images are used, the computational cost may be estimated as: $62\ MN+(35\ MN)(L_1/4+L_2/16+L_3/64+\ldots)$. As described above, computing 30 layers using a traditional auto-focus algorithm results in a total cost of 10.5 billion operations. The cost when using the hierarchical auto-focus algorithm of an embodiment of the present invention, using Li=5, is approximately 1.5 billion operations, which corresponds to a speed increase of 8×. The actual improvement in speed will depend on the particular implementation chosen, wherein accelerations of between 4 and 50× may be achieved in various different implementations.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method comprising:
capturing detector image data for at least a portion of an object under inspection; and
using said detector image data for computing gradient information for at least one depth layer of said at least a portion of said object under inspection without first tomosynthetically reconstructing a plurality of depth layers in which a feature that is of interest potentially resides.

2. The method of claim 1 comprising:
computing gradient information for a plurality of depth layers without first tomosynthetically reconstructing a full image of any afraid plurality of depth layers.

3. The method of claim 2 further comprising:
using the computed gradient information to perform auto-focusing.

4. The method of claim 3 wherein said using the computed gradient information to perform auto-focusing comprises:
evaluating the gradient information for the plurality of depth layers to determine one of said plurality of depth layers that includes an in-focus view of a feature that is of interest.

5. The method of claim 4 wherein said evaluating is performed autonomously by an auto-focus application.

6. The method of claim 1 wherein said using said detector image data for computing said gradient information is performed autonomously by an auto-focus application.

7. The method of claim 1 wherein said using said detector image data for computing said gradient information comprises:
computing a wavelet transform for said captured detector image.

8. The method of claim 7 wherein said wavelet transform comprises a 2D Haar wavelet transform.

9. The method of claim 7 wherein said wavelet transform includes gradient-based image data.

10. The method of claim 9 wherein said wavelet transform includes said gradient-based image data at a plurality of different resolutions.

11. The method of claim 10 wherein said computing said gradient information further comprising:
using said gradient-based image data of a first of said plurality of different resolutions to compute a gradient for at least one of a plurality of depth layers in which a feature of the object under inspection that is of interest potentially resides; and
using said gradient-based image data of a second of said plurality of different resolutions to compute a gradient for at least one of said plurality of depth layers.

12. The method of claim 7 further comprising;
computing said gradient information from said wavelet transform.

13. The method of claim 7 further comprising:
using the wavelet transform to perform auto-focusing.

14. A system comprising:
an auto-focusing processor operable to compute a wavelet transform for a captured detector image of at least a portion of an object under inspection and use the wavelet transform to perform auto-focusing.

15. The system of claim 14 wherein said auto-focusing processor comprises:
computer-executable software code for computing said wavelet transform; and
a processor for executing the computer-executable software code.

16. The system of claim 14 wherein said auto-focusing processor is operable to compute a gradient of a plurality of depth layers of said object under inspection from the wavelet transform.

17. The system of claim 16 wherein said auto-focusing processor is operable to determine from the computed gradient of said plurality of depth layers one of said plurality of depth layers that is most in focus.

18. The system of claim 14 wherein the wavelet transform comprises gradient-based image data at a plurality of different resolutions.

19. The system of claim 18 wherein said auto-focusing processor uses gradient-based image data having a first resolution to determine a region of depth layers of said object under inspection in which a depth layer of interest resides.

20. The system of claim 19 wherein said auto-focusing processor uses gradient-based image data having a finer resolution than said first resolution to determine said depth layer of interest within said region of depth layers.

21. The system of claim 14 wherein said auto-focusing comprises determining a depth layer that is of interest.

22. The system of claim 14 wherein said auto-focusing comprises determining a depth layer that includes an in-focus view of a feature of said object under inspection that is of interest.

23. A system comprising:
means for capturing a detector image of at least a portion of an object under inspection;
means for computing a wavelet transform for said captured detector image;
means for computing a gradient for at least one depth layer of said object under inspection from the wavelet transform; and
means for determining, from gradients of a plurality of different depth layers of said object under inspection, a depth layer that provides an in-focus view of a feature that is of interest.

24. A method comprising:
capturing radiographic image data for at least a portion of an object under inspection; and
performing auto-focusing to determine, from a plurality of depth layers of said object under inspection in which a layer of interest potentially resides, said depth layer of interest, wherein the auto-focusing does not require fully reconstructing all of said plurality of depth layers.

25. The method of claim 24 wherein said auto-focusing does not require fully reconstructing any of said plurality of layers.

26. The method of claim 24 further comprising:
tomosynthetically reconstructing the determined layer of interest after said layer of interest is determined by said auto-focusing.

* * * * *

UNITED STATES PATENT AND TRADEMARK OFFICE
CERTIFICATE OF CORRECTION

PATENT NO.         : 7,424,141 B2
APPLICATION NO. : 10/651667
DATED               : September 9, 2008
INVENTOR(S)       : Gines et al.

It is certified that error appears in the above-identified patent and that said Letters Patent is hereby corrected as shown below:

On the Title Page Item (56), under "Other Publications", line 4, delete "Wavlet" and insert -- Wavelet --, therefor.

On the Title Page Item (56), under "Other Publications", line 9, delete "191." and insert -- 1991. --, therefor.

On the Title Page Item (56), under "Other Publications", line 10, delete "Multicate" and insert -- Multiscale --, therefor.

On the Title Page Item (56), under "Other Publications", line 13, delete "Wacelet" and insert -- Wavelet --, therefor.

In column 31, line 19, in Claim 2, delete "afraid" and insert -- of said --, therefor.

Signed and Sealed this

Thirty-first Day of March, 2009

JOHN DOLL
*Acting Director of the United States Patent and Trademark Office*